US006436898B1

(12) United States Patent
Delcayre

(10) Patent No.: US 6,436,898 B1
(45) Date of Patent: Aug. 20, 2002

(54) COMPOUNDS FOR TREATMENT OF INFECTIOUS AND IMMUNE SYSTEM DISORDERS AND METHODS FOR THEIR USE

(75) Inventor: Alain Delcayre, Auckland (NZ)

(73) Assignee: Genesis Research and Development Corporation Limited, Auckland (NZ)

( * ) Notice: Subject to any disclaimer, the term of this patent is extended or adjusted under 35 U.S.C. 154(b) by 0 days.

(21) Appl. No.: 09/351,348

(22) Filed: Jul. 12, 1999

(51) Int. Cl.[7] ........................ A01N 37/18; A61K 38/00; A61K 39/00; A61K 39/38; C07K 1/00

(52) U.S. Cl. ..................... 514/2; 424/192.1; 424/184.1; 424/248.1; 530/350; 530/388.75

(58) Field of Search ........................... 514/2; 424/192.1, 424/184.1, 248.1; 530/350, 388.15; 536/23.4

(56) References Cited

PUBLICATIONS

Bowie, James U., Science vol. 247, Mar. 16, 1990, pp.1306–1310.*
PCT International Search Report for PCT/NZ00/00121, filed 10 Jul. 2000.
Swiss–Prot Accession No. P91408; Geisel, C. et al., sumitted 15 Dec. 1998.
PIR Accession No. T46707; Ilg, T. et al., submitted 18 Feb. 2000.
PIR Accession No. T28682; Parkhill, J. et al., submitted 15 Oct. 1999.
Trembl Accession No. Q9S9B2; Raghavan, V. et al., submitted 01 May 2000.
Swiss–Prot Accession No. P06530; Kiss, A. et al., submitted 01 Jan. 1988.
Swiss–Prot Accession No. Q06965; Neidle, E.L. et al., submitted 01 Oct. 1996.
TREMBL Accession No. E968234 ; LeGoux, R. et al., submitted Nov. 01, 1998.
TREMBL Accession No. E1263321; Van, L.F. et al., submitted Nov. 01, 1998.
GenPept Accession No. CAB45489; James, K.D. et al., submitted Jun. 18, 1999.
GenPept Accession No. CAB07541; Dziadek, J. et al., submitted Mar. 19, 1997.
GenPept Accession No. BAA97474; Nakamura, Y., submitted Apr. 02, 1999.
Swiss–Prot Accession No. P41014; Ishizuka, M., submitted Aug. 1994.
GenPept Accession No. AAF10382; White, O. et al., submitted Nov. 08, 1999.
GenPept Accession No. AAD34368; Janoir, C., et al., submitted Feb. 22, 1999.
GenPept Accession No. AAC70256; Kuzio, J. et al., submitted Aug. 03, 1998.
GenPept Accession No. AAA72555; Tokunaga, T. et al., submitted 1985.
GenPept Accession No. AAB38132; Shago, M. et al., submitted Feb. 29, 1996.
GenPept Accession No. AAC32046; Zhu, W.M. et al., submitted Nov. 11, 1997.
PCT International Search Report for PCT/NZ00/00121, filed Jul. 10, 2000.
Swiss–Prot Accession No. P91408; Geisel, C. et al., submitted Dec. 15, 1998.
PIR Accession No. T46707; Ilg, T. et al., submitted Feb. 18, 2000.
PIR Accession No. T28682; Parkhill, J. et al., submitted Oct. 15, 1999.
TREMBL Accession No. Q9S9B2; Raghavan, V. et al., submitted May 01, 2000.
Swiss–Prot Accession No. P06530; Kiss, A. et al., submitted Jan. 01, 1998.
Swiss–Prot Accession No. Q06965; Neidle, E.L. et al., submitted Oct. 01, 1996.
TREMBL Accession No. E968234; LeGoux, R. et al., submitted Nov. 01, 1998.
TREMBL Accession No. E1263321; Van, L.F. et al., submitted Nov. 01, 1998.
GenPept Accession No. CAB45489; James, K.D. et al., submitted Jun. 18, 1999.
GenPept Accession No. CAB07541; Dziadek, J. et al., submitted Mar. 19, 1997.
GenPept Accession No. BAA97474; Nakamura, Y., submitted Apr. 02, 1999.
Swiss–Prot Accession No. P41014; Ishizuka, M., submitted Aug. 1994.

* cited by examiner

*Primary Examiner*—Michael C. Wilson
*Assistant Examiner*—Eleanor Sorbello
(74) *Attorney, Agent, or Firm*—Ann W. Speckman; Janet Sleath

(57) ABSTRACT

The present invention provides polypeptides comprising an immunogenic epitope of a *M. vaccae* protein, polynucleotides encoding such polypeptides, and fusion proteins comprising at least one such polypeptide, together with DNA constructs comprising at least one inventive polynucleotide. Compositions comprising such polypeptides, polynucleotides, fusion proteins and/or DNA constructs may be employed in the treatment of infectious diseases and immune disorders.

27 Claims, No Drawings

SEQUENCE LISTING

<160> NUMBER OF SEQ ID NOS: 81

<210> SEQ ID NO 1
<211> LENGTH: 29
<212> TYPE: DNA
<213> ORGANISM: Artificial Sequence
<220> FEATURE:
<223> OTHER INFORMATION: Made in a lab

<400> SEQUENCE: 1
gagagagaaa gcttatggct acaggctcc                              29

<210> SEQ ID NO 2
<211> LENGTH: 30
<212> TYPE: DNA
<213> ORGANISM: Artificial Sequence
<220> FEATURE:
<223> OTHER INFORMATION: Made in a lab

<400> SEQUENCE: 2
aaggaagggg atcccgaagc cacagctgcc                             30

<210> SEQ ID NO 3
<211> LENGTH: 29
<212> TYPE: DNA
<213> ORGANISM: Artificial Sequence
<220> FEATURE:
<223> OTHER INFORMATION: Made in a lab

<400> SEQUENCE: 3
aaggaagggg atccgaagcc acagctgcc                              29

<210> SEQ ID NO 4
<211> LENGTH: 31
<212> TYPE: DNA
<213> ORGANISM: Artificial Sequence
<220> FEATURE:
<223> OTHER INFORMATION: Made in a lab

<400> SEQUENCE: 4
aaggaagggg atcccggaag ccacagctgc c                           31

<210> SEQ ID NO 5
<211> LENGTH: 146
<212> TYPE: DNA
<213> ORGANISM: Mycobacterium vaccae

<400> SEQUENCE: 5
aagcttatgg ctacaggctc ccggacgtcc ctgctcctgg cttttggcct gctctgcctg     60
ccctggcttc aagagggcag tgccttccca accattccct tatccaggct ttttgacaac    120
gctatgcagc tgtggcttcg ggatcc                                        146

<210> SEQ ID NO 6

```
<211> LENGTH: 145
<212> TYPE: DNA
<213> ORGANISM: Mycobacterium vaccae

<400> SEQUENCE: 6
aagcttatgg ctacaggctc ccggacgtcc ctgctcctgg cttttggcct gctctgcctg      60
ccctggcttc aagagggcag tgccttccca accattccct tatccaggct ttttgacaac     120
gctatgcagc tgtggcttcg gatcc                                           145

<210> SEQ ID NO 7
<211> LENGTH: 147
<212> TYPE: DNA
<213> ORGANISM: Mycobacterium vaccae

<400> SEQUENCE: 7
aagcttatgg ctacaggctc ccggacgtcc ctgctcctgg cttttggcct gctctgcctg      60
ccctggcttc aagagggcag tgccttccca accattccct tatccaggct ttttgacaac     120
gctatgcagc tgtggcttcc gggatcc                                         147

<210> SEQ ID NO 8
<211> LENGTH: 39
<212> TYPE: DNA
<213> ORGANISM: Mycobacterium vaccae

<400> SEQUENCE: 8
atcgccgcca ccggcccggt gcccggcacc gcgtggatc                             39

<210> SEQ ID NO 9
<211> LENGTH: 96
<212> TYPE: DNA
<213> ORGANISM: Mycobacterium vaccae

<400> SEQUENCE: 9
gttcgtcagt acccgaagct cttgagagct aaggccaatt gggaagatac ttggaccttc      60
ccatcaatag aggaaaagca tcgccctagg ggatcc                                96

<210> SEQ ID NO 10
<211> LENGTH: 75
<212> TYPE: DNA
<213> ORGANISM: Mycobacterium vaccae

<400> SEQUENCE: 10
gtagcgggcc cggtgtttcg agtgaacttg ggcagggcaa tcccatcgcg cgcagcccgc      60
gcagcggaaa tccac                                                       75

<210> SEQ ID NO 11
<211> LENGTH: 114
<212> TYPE: DNA
<213> ORGANISM: Mycobacterium vaccae

<400> SEQUENCE: 11
atcacgcagg taggccgtcc agccgtactc ttcgccccag aacagcggtg ccgtcgccgc      60
gcagaccagc ggtcctgccg ccagatacac ccaggcggtg gccggcatgt ccag           114

<210> SEQ ID NO 12
<211> LENGTH: 33
<212> TYPE: DNA
<213> ORGANISM: Mycobacterium vaccae

<400> SEQUENCE: 12
```

-continued

```
atcgtggcca gcgcgcgcgg cacggtggag atc                                  33

<210> SEQ ID NO 13
<211> LENGTH: 210
<212> TYPE: DNA
<213> ORGANISM: Mycobacterium vaccae

<400> SEQUENCE: 13
atcgccgcca ccggcccggt gcccggcacc gcgtggatcg ttcgtcagta cccgaagctc      60
ttgagagcta aggccaattg ggaagatact tggaccttcc catcaataga ggaaaagcat     120
cgccctaggg gatccgtagc gggcccggtg tttcgagtga acttgggcag ggcaatccca     180
tcgcgcgcag cccgcgcagc ggaaatccac                                      210

<210> SEQ ID NO 14
<211> LENGTH: 697
<212> TYPE: DNA
<213> ORGANISM: Mycobacterium vaccae

<400> SEQUENCE: 14
atctactcga ccttcgccga ccgggcgtac ccgggtggcc tgacgtactc cggccatccg      60
ctggcgaccg cctgcgcggt cgcgacgatc aacgcgatgg aagacgaagg catggtggcc     120
aacgctgccc gcatcggcga gcaggtgctc ggaccgggtc tgcgcgatct cgccgcccgg     180
caccgttcgg tcggcgaagt ccgcggcctc ggcgtcttct gggcggatct cggtgaggtc     240
gtcctgcggc gactggaatg ccacgttgtt gacgacgatg tccagtccgc caagctgttt     300
caccgtgtcc tcgaccaccg cgcggcagtg cgccggctcg gccaggtcgc cgggcaggcg     360
gaccgcccgc tgtccggcct cttcgatcag tgccagcgca tcccgaaccg cggcggcgta     420
cgcgtcggcg tcggcgccgc gcacggccgg gcacggggcc acctcccgct ccgggcaggc     480
gggtccgtgg accgcagcac ggccgagtcg tttggtacag gtgcgcaccc cgctgaaccg     540
ggccatcagc gccgccgcct cggtcgcgtc gctgcgggac cggaacgggc ccaccgcgct     600
gtcggtgcgc ggcgtgcgga cggtggagaa ccgggggaag ggttcgtcgg tcagcgtcac     660
ccaccaccac cggtgcggga acttcgaccg ccggttg                              697

<210> SEQ ID NO 15
<211> LENGTH: 291
<212> TYPE: DNA
<213> ORGANISM: Mycobacterium vaccae

<400> SEQUENCE: 15
atcagttcgg ccctggtcgc cagcccgccg agggcagcca gttccgctcc ggcgtcgatc      60
gggttgggtc cgtccggcca gcacaccagc atccacccga ggtcgagcaa cgggtccccg     120
acggtgcaca tctcccagtc gatgaacgcc gcgagctcgg ggacgtcgcg gcgcagcagc     180
acgttgttca gatggcagtc gccgtgcatg atcccgggtt cggcgtcgtc gggcctgcgc     240
gagtccagcc agtcggcgag cacatgcacc gacgggaacg actcgggcgc g              291

<210> SEQ ID NO 16
<211> LENGTH: 147
<212> TYPE: DNA
<213> ORGANISM: Mycobacterium vaccae

<400> SEQUENCE: 16
atcacgcagg taggccgtcc agccgtactc ttcgccccag aacagcggtg ccgtcgccgc      60
```

```
gcagaccagc ggtcctgccg ccagatacac ccaggcggtg ccggcatgt ccagatcgtg      120 gccagcgcgc gcggcacggt ggagatc                                          147

<210> SEQ ID NO 17
<211> LENGTH: 138
<212> TYPE: DNA
<213> ORGANISM: Mycobacterium vaccae

<400> SEQUENCE: 17
atcgcgcggc tgtgcgggaa ggacgaggcc gtagcggcgt tgcactacgt cgccccggtt      60
ggcgagaagc aggactacat cgaccgagcc ttgcgcaaca tcgggccgta tctgccagct     120
gaggttcccg ctctcgtc                                                    138

<210> SEQ ID NO 18
<211> LENGTH: 261
<212> TYPE: DNA
<213> ORGANISM: Mycobacterium vaccae

<400> SEQUENCE: 18
gatcggcagg catcacgaac agtaagcggt gttccggttg aatccaatgt gctgtcagca      60
ggcatccgat gccgaacacc gaccacgcga gcagtcgcaa tctgtctcgc gaccctggcg     120
tcacgcggcg tcgtggctcc gcaacccgcc ggcgatgtcc gcgcgccgc tgcggccggc     180 tctccatggc cggttcgttc agtcgctcgt ccggtggctg ttctgcgaac gggcccgccg     240
ccccgtcgtc cgtccgatac g                                                261

<210> SEQ ID NO 19
<211> LENGTH: 279
<212> TYPE: DNA
<213> ORGANISM: Mycobacterium vaccae

<400> SEQUENCE: 19
gatctcgttg cgcgtccgcg agatctgcga ccggtacgac ctgccctaca ccaccgggtc      60
cttcctggcg cagtacggca gtcgtggcg cacgatcgcc aaactgtcgc tgccggacaa     120
gttcctgcgc gacaccgccg acgacgcccc ggagacccgc agcgagcgga tgttcgccga     180
actggatccg tcggagcggc gcgggctgaa gtcggccatc gccgcggtgc ggtcgcgccg     240
gcgcgccaag gtcgctgcga aagccgcgaa gatcgcgat                             279

<210> SEQ ID NO 20
<211> LENGTH: 132
<212> TYPE: DNA
<213> ORGANISM: Mycobacterium vaccae

<400> SEQUENCE: 20
gatccagaac gggccggtct gcgggttgag gtcctcggtg cccagtgccg tcgacgcgac      60
gtcgtcggcg ctggtgatgc ggccgccgta ggcgtcctcg gtccacaacg tcagcaccgt     120
gcccgggcgg at                                                          132

<210> SEQ ID NO 21
<211> LENGTH: 177
<212> TYPE: DNA
<213> ORGANISM: Mycobacterium vaccae

<400> SEQUENCE: 21
gatcagctcg gggagccggg tgcccagcaa cgccagcgtg ggaagcaccg agaccggcgc      60
gatgtgcccg cgcagcagcg cccagccgtg caccccgcgg gaccgggccc gcggaccgc     120
```

```
gtcggagtcg accccggccg ccaccgccgc gcgcgtggtc agcatcagcc acgggat        177
```

<210> SEQ ID NO 22
<211> LENGTH: 15
<212> TYPE: DNA
<213> ORGANISM: Artificial Sequence
<220> FEATURE:
<223> OTHER INFORMATION: Made in a lab

<400> SEQUENCE: 22

```
cgcagctgtg gcttc                                                       15
```

<210> SEQ ID NO 23
<211> LENGTH: 22
<212> TYPE: DNA
<213> ORGANISM: Artificial Sequence
<220> FEATURE:
<223> OTHER INFORMATION: Made in a lab

<400> SEQUENCE: 23

```
ttacttaggt tactagtgga tc                                               22
```

<210> SEQ ID NO 24
<211> LENGTH: 23
<212> TYPE: DNA
<213> ORGANISM: Artificial Sequence
<220> FEATURE:
<223> OTHER INFORMATION: Made in a lab

<400> SEQUENCE: 24

```
cgatctactc gaccttcgcc gac                                              23
```

<210> SEQ ID NO 25
<211> LENGTH: 24
<212> TYPE: DNA
<213> ORGANISM: Artificial Sequence
<220> FEATURE:
<223> OTHER INFORMATION: Made in a lab

<400> SEQUENCE: 25

```
ttacgcccag aagacgccga ggcc                                             24
```

<210> SEQ ID NO 26
<211> LENGTH: 26
<212> TYPE: DNA
<213> ORGANISM: Artificial Sequence
<220> FEATURE:
<223> OTHER INFORMATION: Made in a lab

<400> SEQUENCE: 26

```
gatcccatca ccatcaccat cactga                                           26
```

<210> SEQ ID NO 27
<211> LENGTH: 26
<212> TYPE: DNA
<213> ORGANISM: Artificial Sequence
<220> FEATURE:
<223> OTHER INFORMATION: Made in a lab

<400> SEQUENCE: 27

```
ggtagtggta gtggtagtga ctttaa                                           26
```

<210> SEQ ID NO 28
<211> LENGTH: 20
<212> TYPE: DNA

```
<213> ORGANISM: Artificial Sequence
<220> FEATURE:
<223> OTHER INFORMATION: Made in a lab

<400> SEQUENCE: 28
atggctacag gctcccggac                                                     20

<210> SEQ ID NO 29
<211> LENGTH: 34
<212> TYPE: DNA
<213> ORGANISM: Artificial Sequence
<220> FEATURE:
<223> OTHER INFORMATION: Made in a lab

<400> SEQUENCE: 29
gagagagaga tctgtggatt tccgctgcgc gggc                                     34

<210> SEQ ID NO 30
<211> LENGTH: 34
<212> TYPE: DNA
<213> ORGANISM: Artificial Sequence
<220> FEATURE:
<223> OTHER INFORMATION: Made in a lab

<400> SEQUENCE: 30
gagagagaga tctcgcgccc gagtcgttcc cgtc                                     34

<210> SEQ ID NO 31
<211> LENGTH: 34
<212> TYPE: DNA
<213> ORGANISM: Artificial Sequence
<220> FEATURE:
<223> OTHER INFORMATION: Made in a lab

<400> SEQUENCE: 31
gagagagaga tctgatctcc accgtgccgc gcgc                                     34

<210> SEQ ID NO 32
<211> LENGTH: 34
<212> TYPE: DNA
<213> ORGANISM: Artificial Sequence
<220> FEATURE:
<223> OTHER INFORMATION: Made in a lab

<400> SEQUENCE: 32
gagagagaga tctgacgaga gcgggaacct cagc                                     34

<210> SEQ ID NO 33
<211> LENGTH: 34
<212> TYPE: DNA
<213> ORGANISM: Artificial Sequence
<220> FEATURE:
<223> OTHER INFORMATION: Made in a lab

<400> SEQUENCE: 33
gagagagaga tctatcgcga tcttcgcggc tttc                                     34

<210> SEQ ID NO 34
<211> LENGTH: 34
<212> TYPE: DNA
<213> ORGANISM: Artificial Sequence
<220> FEATURE:
<223> OTHER INFORMATION: Made in a lab

<400> SEQUENCE: 34
gagagagaga tctatccgcc cgggcacggt gctg                                     34
```

-continued

```
<210> SEQ ID NO 35
<211> LENGTH: 34
<212> TYPE: DNA
<213> ORGANISM: Artificial Sequence
<220> FEATURE:
<223> OTHER INFORMATION: Made in a lab

<400> SEQUENCE: 35
gagagagaga tctatcccgt ggctgatgct gacc                            34

<210> SEQ ID NO 36
<211> LENGTH: 36
<212> TYPE: DNA
<213> ORGANISM: Artificial Sequence
<220> FEATURE:
<223> OTHER INFORMATION: Made in a lab

<400> SEQUENCE: 36
gagagagaga tctcgtatcg gacggacgac gggacg                          36

<210> SEQ ID NO 37
<211> LENGTH: 35
<212> TYPE: DNA
<213> ORGANISM: Artificial Sequence
<220> FEATURE:
<223> OTHER INFORMATION: Made in a lab

<400> SEQUENCE: 37
gagagagagg atcccaaccg gcggtcgaag ttccc                           35

<210> SEQ ID NO 38
<211> LENGTH: 36
<212> TYPE: DNA
<213> ORGANISM: Artificial Sequence
<220> FEATURE:
<223> OTHER INFORMATION: Made in a lab

<400> SEQUENCE: 38
aaggaaggaa aaggatccgg gaatggttgg gaaggc                          36

<210> SEQ ID NO 39
<211> LENGTH: 126
<212> TYPE: DNA
<213> ORGANISM: Artificial Sequence
<220> FEATURE:
<223> OTHER INFORMATION: Made in a lab

<400> SEQUENCE: 39
aagcttatgg ctacaggctc ccggacgtcc ctgctcctgg cttttggcct gctctgcctg    60
ccctggcttc aagagggcag tgccttccca accattcccg atcccacca tcatcaccat   120 cactga                                                            126

<210> SEQ ID NO 40
<211> LENGTH: 35
<212> TYPE: DNA
<213> ORGANISM: Artificial Sequence
<220> FEATURE:
<223> OTHER INFORMATION: Made in a lab

<400> SEQUENCE: 40
gagagagaga tctatctact cgaccttcgc cgacc                           35

<210> SEQ ID NO 41
```

```
<211> LENGTH: 37
<212> TYPE: DNA
<213> ORGANISM: Artificial Sequence
<220> FEATURE:
<223> OTHER INFORMATION: Made in a lab

<400> SEQUENCE: 41
aaggaaggaa ggatcccgcc cagaagacgc cgaggcc                                    37

<210> SEQ ID NO 42
<211> LENGTH: 34
<212> TYPE: DNA
<213> ORGANISM: Artificial Sequence
<220> FEATURE:
<223> OTHER INFORMATION: Made in a lab

<400> SEQUENCE: 42
gagagagaga tctatcagtt cggccctggt cgcc                                       34

<210> SEQ ID NO 43
<211> LENGTH: 37
<212> TYPE: DNA
<213> ORGANISM: Artificial Sequence
<220> FEATURE:
<223> OTHER INFORMATION: Made in a lab

<400> SEQUENCE: 43
aaggaaggaa ggatcccgcg cccgagtcgt tcccgtc                                    37

<210> SEQ ID NO 44
<211> LENGTH: 35
<212> TYPE: DNA
<213> ORGANISM: Artificial Sequence
<220> FEATURE:
<223> OTHER INFORMATION: Made in a lab

<400> SEQUENCE: 44
gagagagaga tctgatcggc aggcatcacg aacag                                      35

<210> SEQ ID NO 45
<211> LENGTH: 37
<212> TYPE: DNA
<213> ORGANISM: Artificial Sequence
<220> FEATURE:
<223> OTHER INFORMATION: Made in a lab

<400> SEQUENCE: 45
aaggaaggaa ggatcccgta tcggacggac gacgggg                                    37

<210> SEQ ID NO 46
<211> LENGTH: 34
<212> TYPE: DNA
<213> ORGANISM: Artificial Sequence
<220> FEATURE:
<223> OTHER INFORMATION: Made in a lab

<400> SEQUENCE: 46
gagagagaga tctgatccag aacgggccgg tctg                                       34

<210> SEQ ID NO 47
<211> LENGTH: 37
<212> TYPE: DNA
<213> ORGANISM: Artificial Sequence
<220> FEATURE:
<223> OTHER INFORMATION: Made in a lab

<400> SEQUENCE: 47
```
aaggaaggaa ggatccatcc gcccgggcac ggtgctg                            37

<210> SEQ ID NO 48
<211> LENGTH: 35
<212> TYPE: DNA
<213> ORGANISM: Artificial Sequence
<220> FEATURE:
<223> OTHER INFORMATION: Made in a lab

<400> SEQUENCE: 48
gagagagaga tctgatcagc tcggggagcc gggtg                              35

<210> SEQ ID NO 49
<211> LENGTH: 37
<212> TYPE: DNA
<213> ORGANISM: Artificial Sequence
<220> FEATURE:
<223> OTHER INFORMATION: Made in a lab

<400> SEQUENCE: 49
aaggaaggaa ggatccatcc cgtggctgat gctgacc                            37

<210> SEQ ID NO 50
<211> LENGTH: 22
<212> TYPE: DNA
<213> ORGANISM: Artificial Sequence
<220> FEATURE:
<223> OTHER INFORMATION: Made in a lab

<400> SEQUENCE: 50
tatcgccgcc accggcccgg tg                                            22

<210> SEQ ID NO 51
<211> LENGTH: 22
<212> TYPE: DNA
<213> ORGANISM: Artificial Sequence
<220> FEATURE:
<223> OTHER INFORMATION: Made in a lab

<400> SEQUENCE: 51
cgtggatttc cgctgcgcgg gc                                            22

<210> SEQ ID NO 52
<211> LENGTH: 33
<212> TYPE: DNA
<213> ORGANISM: Artificial Sequence
<220> FEATURE:
<223> OTHER INFORMATION: Made in a lab

<400> SEQUENCE: 52
gagagagaga tctatcacgc aggtaggccg tcc                                33

<210> SEQ ID NO 53
<211> LENGTH: 37
<212> TYPE: DNA
<213> ORGANISM: Artificial Sequence
<220> FEATURE:
<223> OTHER INFORMATION: Made in a lab

<400> SEQUENCE: 53
aaggaaggaa ggatccgatc tccaccgtgc cgcgcgc                            37

<210> SEQ ID NO 54
<211> LENGTH: 35
<212> TYPE: DNA

<210> SEQ ID NO 55
<211> LENGTH: 37
<212> TYPE: DNA
<213> ORGANISM: Artificial Sequence
<220> FEATURE:
<223> OTHER INFORMATION: Made in a lab

<400> SEQUENCE: 54
gagagagaga tctatcgcgc ggctgtgcgg gaagg                        35

<210> SEQ ID NO 55
<211> LENGTH: 37
<212> TYPE: DNA
<213> ORGANISM: Artificial Sequence
<220> FEATURE:
<223> OTHER INFORMATION: Made in a lab

<400> SEQUENCE: 55
aaggaaggaa ggatccgacg agagcgggaa cctcagc                      37

<210> SEQ ID NO 56
<211> LENGTH: 1749
<212> TYPE: DNA
<213> ORGANISM: Artificial Sequence
<220> FEATURE:
<223> OTHER INFORMATION: Made in a lab

<400> SEQUENCE: 56
atggctacag gctcccggac gtccctgctc ctggcttttg gcctgctctg cctgccctgg      60
cttcaagagg gcagtgcctt cccaaccatt cccggatcta tctactcgac cttcgccgac    120
cgggcgtacc cggtggcct gacgtactcc ggccatccgc tggcgaccgc ctgcgcggtc     180
gcgacgatca acgcgatgga agacgaaggc atggtggcca acgctgcccg catcggcgag    240
caggtgctcg gaccgggtct gcgcgatctc gccgcccggc accgttcggt cggcgaagtc    300
cgcggcctcg gcgtcttctg gcgggatct gatccagaac gggccggtct gcgggttgag     360
gtcctcggtg cccagtgccg tcgacgcgac gtcgtcggcg ctggtgatgc ggccgccgta    420
ggcgtcctcg gtccacaacg tcagcaccgt gcccgggcgg atggatctga tcggcaggca    480
tcacgaacag taagcggtgt tccggttgaa tccaatgtgc tgtcagcagg catccgatgc    540
cgaacaccga ccacgcgagc agtcgcaatc tgtctcgcga ccctggcgtc acgcggcgtc    600
gtggctccgc aacccgccgg cgatgtcgcg cgcgccgctg cggccggctc tccatggccg    660
gttcgttcag tcgctcgtcc ggtggctgtt ctgcgaacgg gcccgccgcc cgtcgtccg     720 tccgatacgg gatctgatca gctcggggag ccgggtgccc agcaacgcca gcgtgggaag    780
caccgagacc ggcgcgatgt gcccgcgcag cagcgcccag ccgtgcaccc cgcgggaccg    840
ggccccgcgg accgcgtcgg agtcgacccc ggccgccacc gccgcgcgcg tggtcagcat    900
cagccacggg atggatctat cagttcggcc ctggtcgcca gcccgccgag ggcagccagt    960
tccgctccgg cgtcgatcgg gttgggtccg tccggccagc acaccagcat ccacccgagg   1020
tcgagcaacg ggtccccgac ggtgcacatc tcccagtcga tgaacgccgc gagctcgggg   1080
acgtcgcggc gcagcagcac gttgttcaga tggcagtcgc cgtgcatgat cccgggttcg   1140
gcgtcgtcgg gcctgcgcga gtccagccag tcggcagca catgcaccga cgggaacgac    1200
tcgggcgcgg gatctatcac gcaggtaggc cgtccagccg tactcttcgc cccagaacag    1260
cggtgccgtc gccgcgcaga ccagcggtcc tgccgccaga tacccaggcg gtggccgg    1320 catgtccaga tcgtggccag cgcgcgcggc acgtggaga tcggatctat cgcgcggctg     1380
tgcgggaagg acgaggccgt agcggcgttg cactacgtcg ccccggttgg cgagaagcag   1440
gactacatcg accgagcctt gcgcaacatc gggccgtatc tgccagctga ggttcccgct   1500

| | |
|---|---|
| ctcgtcggat ctatcgccgc caccggcccg gtgcccggca ccgcgtggat cgttcgtcag | 1560 |
| tacccgaagc tcttgagagc taaggccaat tgggaagata cttggacctt cccatcaata | 1620 |
| gaggaaaagc atcgccctag ggatccgta gcgggcccgg tgtttcgagt gaacttgggc | 1680 |
| agggcaatcc catcgcgcgc agcccgcgca gcggaaatcc acggatccca tcaccatcac | 1740 |
| catcactga | 1749 |

<210> SEQ ID NO 57
<211> LENGTH: 1749
<212> TYPE: DNA
<213> ORGANISM: Artificial Sequence
<220> FEATURE:
<223> OTHER INFORMATION: Made in a lab

<400> SEQUENCE: 57

| | |
|---|---|
| atggctacag gtcccgac gtccctgctc ctggcttttg gcctgctctg cctgccctgg | 60 |
| cttcaagagg gcagtgcctt cccaaccatt cccggatcta tctactcgac cttcgccgac | 120 |
| cgggcgtacc cggtggcct gacgtactcc ggccatccgc tggcgaccgc ctgcgcggtc | 180 |
| gcgacgatca acgcgatgga agacgaaggc atggtggcca acgctgcccg catcggcgag | 240 |
| caggtgctcg gaccgggtct gcgcgatctc ccgcccggc accgttcggt cggcgaagtc | 300 |
| cgcggcctcg gcgtcttctg gcgggatct atcagttcgg ccctggtcgc cagcccgccg | 360 |
| agggcagcca gttccgctcc ggcgtcgatc gggttgggtc cgtccggcca gcacaccagc | 420 |
| atccacccga ggtcgagcaa cgggtccccg acggtgcaca tctcccagtc gatgaacgcc | 480 |
| gcgagctcgg ggacgtcgcg gcgcagcagc acgttgttca gatggcagtc gccgtgcatg | 540 |
| atcccgggtt cggcgtcgtc gggcctgcgc gagtccagcc agtcggcgag cacatgcacc | 600 |
| gacgggaacg actcgggcgc gggatctgat cggcaggcat cacgaacagt aagcggtgtt | 660 |
| ccggttgaat ccaatgtgct gtcagcaggc atccgatgcc gaacaccgac cacgcgagca | 720 |
| gtcgcaatct gtctcgcgac cctggcgtca cgcggcgtcg tggctccgca acccgccggc | 780 |
| gatgtcgcgc gcgccgctgc ggccggctct ccatggccgg ttcgttcagt cgctcgtccg | 840 |
| gtggctgttc tgcgaacggg cccgccgccc cgtcgtccgt ccgatacggg atctgatcag | 900 |
| ctcggggagc cgggtgccca gcaacgccag cgtgggaagc accgagaccg gcgcgatgtg | 960 |
| cccgcgcagc agcgcccagc cgtgcacccc gcgggaccgg gccccgcgga ccgcgtcgga | 1020 |
| gtcgaccccg gccgccaccg ccgcgcgcgt ggtcagcatc agccacggga tggatctatc | 1080 |
| acgcaggtag gccgtccagc cgtactcttc gccccagaac agcggtgccg tcgccgcgca | 1140 |
| gaccagcggt cctgccgcca gatacaccca ggcggtggcc ggcatgtcca gatcgtggcc | 1200 |
| agcgcgcgcg gcacggtgga gatcggatct atcgcgcggc tgtgcgggaa ggacgaggcc | 1260 |
| gtagcggcgt tgcactacgt cgcccggtt ggcgagaagc aggactacat cgaccgagcc | 1320 |
| ttgcgcaaca tcgggccgta tctgccagct gaggttcccg ctctcgtcgg atctgatcca | 1380 |
| gaacgggccg gtctgcgggt tgaggtcctc ggtgcccagt gccgtcgacg cgacgtcgtc | 1440 |
| ggcgctggtg atgcggccgc cgtaggcgtc ctcggtccac aacgtcagca ccgtgcccgg | 1500 |
| gcggatggat ctatcgccgc caccggcccg gtgcccggca ccgcgtggat cgttcgtcag | 1560 |
| tacccgaagc tcttgagagc taaggccaat tgggaagata cttggacctt cccatcaata | 1620 |
| gaggaaaagc atcgccctag ggatccgta gcgggcccgg tgtttcgagt gaacttgggc | 1680 |
| agggcaatcc catcgcgcgc agcccgcgca gcggaaatcc acggatccca tcaccatcac | 1740 |

-continued

|  |  |
|---|---:|
| catcactga | 1749 |

<210> SEQ ID NO 58
<211> LENGTH: 1749
<212> TYPE: DNA
<213> ORGANISM: Artificial Sequence
<220> FEATURE:
<223> OTHER INFORMATION: Made in a lab

<400> SEQUENCE: 58

| | |
|---|---:|
| atggctacag gctcccggac gtccctgctc ctggcttttg gcctgctctg cctgccctgg | 60 |
| cttcaagagg gcagtgcctt cccaaccatt cccggatcta tctactcgac cttcgccgac | 120 |
| cgggcgtacc cgggtggcct gacgtactcc ggccatccgc tggcgaccgc ctgcgcggtc | 180 |
| gcgacgatca acgcgatgga agacgaaggc atggtggcca acgctgcccg catcggcgag | 240 |
| caggtgctcg gaccgggtct gcgcgatctc gccgcccggc accgttcggt cggcgaagtc | 300 |
| cgcggcctcg gcgtcttctg gcgggatct gatccagaac gggccggtct gcgggttgag | 360 |
| gtcctcggtg cccagtgccg tcgacgcgac gtcgtcggcg ctggtgatgc ggccgccgta | 420 |
| ggcgtcctcg gtccacaacg tcagcaccgt gcccgggcg atggatctat cagttcggcc | 480 |
| ctggtcgcca gcccgccgag ggcagccagt tccgctccgg cgtcgatcgg gttgggtccg | 540 |
| tccggccagc acaccagcat ccacccgagg tcgagcaacg ggtccccgac ggtgcacatc | 600 |
| tcccagtcga tgaacgccgc gagctcgggg acgtcgcggc gcagcagcac gttgttcaga | 660 |
| tggcagtcgc cgtgcatgat cccgggttcg gcgtcgtcgg gcctgcgcga gtccagccag | 720 |
| tcggcgagca catgcaccga cgggaacgac tcgggcgcgg gatctgatca gctcggggag | 780 |
| ccgggtgccc agcaacgcca gcgtgggaag caccgagacc ggcgcgatgt gcccgcgcag | 840 |
| cagcgcccag ccgtgcaccc cgcgggaccg ggccccgcgg accgcgtcgg agtcgacccc | 900 |
| ggccgccacc gccgcgcgcg tggtcagcat cagccacgg atggatctga tcggcaggca | 960 |
| tcacgaacag taagcggtgt tccggttgaa tccaatgtgc tgtcagcagg catccgatgc | 1020 |
| cgaacaccga ccacgcgagc agtcgcaatc tgtctcgcga ccctggcgtc acgcggcgtc | 1080 |
| gtggctccgc aacccgccgg cgatgtcgcg cgcgccgctg cggccggctc tccatggccg | 1140 |
| gttcgttcag tcgctcgtcc ggtggctgtt ctgcgaacgg gcccgccgcc ccgtcgtccg | 1200 |
| tccgatacgg gatctatcac gcaggtaggc cgtccagccg tactcttcgc cccagaacag | 1260 |
| cggtgccgtc gccgcgcaga ccagcggtcc tgccgccaga tacacccagg cggtggccgg | 1320 |
| catgtccaga tcgtggccag cgcgcgcggc acggtggaga tcggatctat cgcgcggctg | 1380 |
| tgcgggaagg acgaggccgt agcggcgttg cactacgtcg ccccggttgg cgagaagcag | 1440 |
| gactacatcg accgagcctt gcgcaacatc gggccgtatc tgccagctga ggttcccgct | 1500 |
| ctcgtcggat ctatcgccgc caccggcccg gtgcccggca ccgcgtggat cgttcgtcag | 1560 |
| tacccgaagc tcttgagagc taaggccaat tgggaagata cttggacctt cccatcaata | 1620 |
| gaggaaaagc atcgccctag gggatccgta gcgggcccgg tgtttcgagt gaacttgggc | 1680 |
| agggcaatcc catcgcgcgc agcccgcgca gcggaaatcc acggatccca tcaccatcac | 1740 |
| catcactga | 1749 |

<210> SEQ ID NO 59
<211> LENGTH: 23
<212> TYPE: DNA
<213> ORGANISM: Artificial Sequence
<220> FEATURE:
<223> OTHER INFORMATION: Made in a lab

```
<400> SEQUENCE: 59
cgatctactc gaccttcgcc gac                                    23

<210> SEQ ID NO 60
<211> LENGTH: 24
<212> TYPE: DNA
<213> ORGANISM: Artificial Sequence
<220> FEATURE:
<223> OTHER INFORMATION: Made in a lab

<400> SEQUENCE: 60
tcagtggatt tccgctgcgc gggc                                   24

<210> SEQ ID NO 61
<211> LENGTH: 46
<212> TYPE: PRT
<213> ORGANISM: Mycobacterium vaccae

<400> SEQUENCE: 61

Met Ala Thr Gly Ser Arg Thr Ser Leu Leu Ala Phe Gly Leu Leu
 1               5                  10                  15

Cys Leu Pro Trp Leu Gln Glu Gly Ser Ala Phe Pro Thr Ile Pro Leu
            20                  25                  30

Ser Arg Leu Phe Asp Asn Ala Met Gln Leu Trp Leu Arg Asp
        35                  40                  45

<210> SEQ ID NO 62
<211> LENGTH: 46
<212> TYPE: PRT
<213> ORGANISM: Mycobacterium vaccae

<400> SEQUENCE: 62

Met Ala Thr Gly Ser Arg Thr Ser Leu Leu Ala Phe Gly Leu Leu
 1               5                  10                  15

Cys Leu Pro Trp Leu Gln Glu Gly Ser Ala Phe Pro Thr Ile Pro Leu
            20                  25                  30

Ser Arg Leu Phe Asp Asn Ala Met Gln Leu Trp Leu Arg Ile
        35                  40                  45

<210> SEQ ID NO 63
<211> LENGTH: 46
<212> TYPE: PRT
<213> ORGANISM: Mycobacterium vaccae

<400> SEQUENCE: 63

Met Ala Thr Gly Ser Arg Thr Ser Leu Leu Ala Phe Gly Leu Leu
 1               5                  10                  15

Cys Leu Pro Trp Leu Gln Glu Gly Ser Ala Phe Pro Thr Ile Pro Leu
            20                  25                  30

Ser Arg Leu Phe Asp Asn Ala Met Gln Leu Trp Leu Pro Gly
        35                  40                  45

<210> SEQ ID NO 64
<211> LENGTH: 13
<212> TYPE: PRT
<213> ORGANISM: Mycobacterium vaccae

<400> SEQUENCE: 64

Ile Ala Ala Thr Gly Pro Val Pro Gly Thr Ala Trp Ile
 1               5                  10
```

```
<210> SEQ ID NO 65
<211> LENGTH: 32
<212> TYPE: PRT
<213> ORGANISM: Mycobacterium vaccae

<400> SEQUENCE: 65

Val Arg Gln Tyr Pro Lys Leu Leu Arg Ala Lys Ala Asn Trp Glu Asp
 1               5                  10                  15

Thr Trp Thr Phe Pro Ser Ile Glu Glu Lys His Arg Pro Arg Gly Ser
            20                  25                  30

<210> SEQ ID NO 66
<211> LENGTH: 25
<212> TYPE: PRT
<213> ORGANISM: Mycobacterium vaccae

<400> SEQUENCE: 66

Val Ala Gly Pro Val Phe Arg Val Asn Leu Gly Arg Ala Ile Pro Ser
 1               5                  10                  15

Arg Ala Ala Arg Ala Ala Glu Ile His
            20                  25

<210> SEQ ID NO 67
<211> LENGTH: 38
<212> TYPE: PRT
<213> ORGANISM: Mycobacterium vaccae

<400> SEQUENCE: 67

Ile Thr Gln Val Gly Arg Pro Ala Val Leu Phe Ala Pro Glu Gln Arg
 1               5                  10                  15

Cys Arg Arg Arg Ala Asp Gln Arg Ser Cys Arg Gln Ile His Pro Gly
            20                  25                  30

Gly Gly Arg His Val Gln
         35

<210> SEQ ID NO 68
<211> LENGTH: 11
<212> TYPE: PRT
<213> ORGANISM: Mycobacterium vaccae

<400> SEQUENCE: 68

Ile Val Ala Ser Ala Arg Gly Thr Val Glu Ile
 1               5                  10

<210> SEQ ID NO 69
<211> LENGTH: 70
<212> TYPE: PRT
<213> ORGANISM: Mycobacteerium vaccae

<400> SEQUENCE: 69

Ile Ala Ala Thr Gly Pro Val Pro Gly Thr Ala Trp Ile Val Arg Gln
 1               5                  10                  15

Tyr Pro Lys Leu Leu Arg Ala Lys Ala Asn Trp Glu Asp Thr Trp Thr
            20                  25                  30

Phe Pro Ser Ile Glu Glu Lys His Arg Pro Arg Gly Ser Val Ala Gly
         35                  40                  45

Pro Val Phe Arg Val Asn Leu Gly Arg Ala Ile Pro Ser Arg Ala Ala
     50                  55                  60

Arg Ala Ala Glu Ile His
65                  70
```

-continued

```
<210> SEQ ID NO 70
<211> LENGTH: 75
<212> TYPE: PRT
<213> ORGANISM: Mycobacterium vaccae

<400> SEQUENCE: 70
```

Ile Tyr Ser Thr Phe Ala Asp Arg Ala Tyr Pro Gly Gly Leu Thr Tyr
1               5                  10                  15

Ser Gly His Pro Leu Ala Thr Ala Cys Ala Val Ala Thr Ile Asn Ala
            20                  25                  30

Met Glu Asp Glu Gly Met Val Ala Asn Ala Ala Arg Ile Gly Glu Gln
        35                  40                  45

Val Leu Gly Pro Gly Leu Arg Asp Leu Ala Ala Arg His Arg Ser Val
    50                  55                  60

Gly Glu Val Arg Gly Leu Gly Val Phe Trp Ala
65                  70                  75

```
<210> SEQ ID NO 71
<211> LENGTH: 97
<212> TYPE: PRT
<213> ORGANISM: Mycobacterium vaccae

<400> SEQUENCE: 71
```

Ile Ser Ser Ala Leu Val Ala Ser Pro Pro Arg Ala Ala Ser Ser Ala
1               5                  10                  15

Pro Ala Ser Ile Gly Leu Gly Pro Ser Gly Gln His Thr Ser Ile His
            20                  25                  30

Pro Arg Ser Ser Asn Gly Ser Pro Thr Val His Ile Ser Gln Ser Met
        35                  40                  45

Asn Ala Ala Ser Ser Gly Thr Ser Arg Arg Ser Ser Thr Leu Phe Arg
    50                  55                  60

Trp Gln Ser Pro Cys Met Ile Pro Gly Ser Ala Ser Ser Gly Leu Arg
65                  70                  75                  80

Glu Ser Ser Gln Ser Ala Ser Thr Cys Thr Asp Gly Asn Asp Ser Gly
                85                  90                  95

Ala

```
<210> SEQ ID NO 72
<211> LENGTH: 49
<212> TYPE: PRT
<213> ORGANISM: Mycobacterium vaccae

<400> SEQUENCE: 72
```

Ile Thr Gln Val Gly Arg Pro Ala Val Leu Phe Ala Pro Glu Gln Arg
1               5                  10                  15

Cys Arg Arg Arg Ala Asp Gln Arg Ser Cys Arg Gln Ile His Pro Gly
            20                  25                  30

Gly Gly Arg His Val Gln Ile Val Ala Ser Ala Arg Gly Thr Val Glu
        35                  40                  45

Ile

```
<210> SEQ ID NO 73
<211> LENGTH: 46
<212> TYPE: PRT
<213> ORGANISM: Mycobacterium vaccae

<400> SEQUENCE: 73
```

Ile Ala Arg Leu Cys Gly Lys Asp Glu Ala Val Ala Ala Leu His Tyr

```
                1               5                  10                 15
Val Ala Pro Val Gly Glu Lys Gln Asp Tyr Ile Asp Arg Ala Leu Arg
                                20                 25                 30

Asn Ile Gly Pro Tyr Leu Pro Ala Glu Val Pro Ala Leu Val
                35                 40                 45

<210> SEQ ID NO 74
<211> LENGTH: 87
<212> TYPE: PRT
<213> ORGANISM: Mycobacterium vaccae

<400> SEQUENCE: 74

Asp Arg Gln Ala Ser Arg Thr Val Ser Gly Val Pro Val Glu Ser Asn
1               5                  10                 15

Val Leu Ser Ala Gly Ile Arg Cys Arg Thr Pro Thr Thr Arg Ala Val
                20                 25                 30

Ala Ile Cys Leu Ala Thr Leu Ala Ser Arg Gly Val Val Ala Pro Gln
                35                 40                 45

Pro Ala Gly Asp Val Ala Arg Ala Ala Ala Gly Ser Pro Trp Pro
        50                 55                 60

Val Arg Ser Val Ala Arg Pro Val Ala Val Leu Arg Thr Gly Pro Pro
65                  70                 75                      80

Pro Arg Arg Pro Ser Asp Thr
                85

<210> SEQ ID NO 75
<211> LENGTH: 93
<212> TYPE: PRT
<213> ORGANISM: Mycobacterium vaccae

<400> SEQUENCE: 75

Asp Leu Val Ala Arg Pro Arg Asp Leu Arg Pro Val Arg Pro Ala Leu
1               5                  10                 15

His His Arg Val Leu Pro Gly Ala Val Arg Gln Val Val Ala His Asp
                20                 25                 30

Arg Glu Thr Val Ala Ala Gly Gln Val Pro Ala Arg His Arg Arg Arg
                35                 40                 45

Arg Pro Gly Asp Pro Gln Arg Ala Asp Val Arg Arg Thr Gly Ser Val
        50                 55                 60

Gly Ala Arg Ala Glu Val Gly His Arg Arg Gly Ala Val Ala Pro
65                  70                 75                      80

Ala Arg Gln Gly Arg Cys Glu Ser Arg Glu Asp Arg Asp
                85                 90

<210> SEQ ID NO 76
<211> LENGTH: 44
<212> TYPE: PRT
<213> ORGANISM: Mycobacterium vaccae

<400> SEQUENCE: 76

Asp Pro Glu Arg Ala Gly Leu Arg Val Glu Val Leu Gly Ala Gln Cys
1               5                  10                 15

Arg Arg Arg Asp Val Val Gly Ala Gly Asp Ala Ala Val Gly Val
                20                 25                 30

Leu Gly Pro Gln Arg Gln His Arg Ala Arg Ala Asp
                35                 40

<210> SEQ ID NO 77
```

```
<211> LENGTH: 59
<212> TYPE: PRT
<213> ORGANISM: Mycobacterium vaccae

<400> SEQUENCE: 77

Asp Gln Leu Gly Glu Pro Gly Ala Gln Gln Arg Gln Arg Gly Lys His
1               5                   10                  15

Arg Asp Arg Arg Asp Val Pro Ala Gln Gln Arg Pro Ala Val His Pro
            20                  25                  30

Ala Gly Pro Gly Pro Ala Asp Arg Val Gly Val Asp Pro Gly Arg His
        35                  40                  45

Arg Arg Ala Arg Gly Gln His Gln Pro Arg Asp
    50                  55

<210> SEQ ID NO 78
<211> LENGTH: 39
<212> TYPE: PRT
<213> ORGANISM: Artificial Sequence
<220> FEATURE:
<223> OTHER INFORMATION: Made in a lab

<400> SEQUENCE: 78

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Gly
            20                  25                  30

Ser His His His His His His
        35

<210> SEQ ID NO 79
<211> LENGTH: 582
<212> TYPE: PRT
<213> ORGANISM: Artificial Sequence
<220> FEATURE:
<223> OTHER INFORMATION: Made in a lab

<400> SEQUENCE: 79

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Gly
            20                  25                  30

Ser Ile Tyr Ser Thr Phe Ala Asp Arg Ala Tyr Pro Gly Gly Leu Thr
        35                  40                  45

Tyr Ser Gly His Pro Leu Ala Thr Ala Cys Ala Val Ala Thr Ile Asn
    50                  55                  60

Ala Met Glu Asp Glu Gly Met Val Ala Asn Ala Ala Arg Ile Gly Glu
65                  70                  75                  80

Gln Val Leu Gly Pro Gly Leu Arg Asp Leu Ala Ala Arg His Arg Ser
                85                  90                  95

Val Gly Glu Val Arg Gly Leu Gly Val Phe Trp Ala Gly Ser Asp Pro
            100                 105                 110

Glu Arg Ala Gly Leu Arg Val Glu Val Leu Gly Ala Gln Cys Arg Arg
        115                 120                 125

Arg Asp Val Val Gly Ala Gly Asp Ala Ala Val Gly Val Leu Gly
    130                 135                 140

Pro Gln Arg Gln His Arg Ala Arg Ala Asp Gly Ser Asp Arg Gln Ala
145                 150                 155                 160

Ser Arg Thr Val Ser Gly Val Pro Val Glu Ser Asn Val Leu Ser Ala
                165                 170                 175
```

```
Gly Ile Arg Cys Arg Thr Pro Thr Arg Ala Val Ala Ile Cys Leu
            180                 185                 190

Ala Thr Leu Ala Ser Arg Gly Val Val Ala Pro Gln Pro Ala Gly Asp
        195                 200                 205

Val Ala Arg Ala Ala Ala Ala Gly Ser Pro Trp Pro Val Arg Ser Val
        210                 215                 220

Ala Arg Pro Val Ala Val Leu Arg Thr Gly Pro Pro Arg Arg Pro
225                 230                 235                 240

Ser Asp Thr Gly Ser Asp Gln Leu Gly Glu Pro Gly Ala Gln Gln Arg
            245                 250                 255

Gln Arg Gly Lys His Arg Asp Arg Arg Asp Val Pro Ala Gln Gln Arg
            260                 265                 270

Pro Ala Val His Pro Ala Gly Pro Gly Pro Ala Asp Arg Val Gly Val
            275                 280                 285

Asp Pro Gly Arg His Arg Arg Ala Arg Gly Gln His Gln Pro Arg Asp
            290                 295                 300

Gly Ser Ile Ser Ser Ala Leu Val Ala Ser Pro Pro Arg Ala Ala Ser
305                 310                 315                 320

Ser Ala Pro Ala Ser Ile Gly Leu Gly Pro Ser Gly Gln His Thr Ser
            325                 330                 335

Ile His Pro Arg Ser Ser Asn Gly Ser Pro Thr Val His Ile Ser Gln
            340                 345                 350

Ser Met Asn Ala Ala Ser Ser Gly Thr Ser Arg Arg Ser Ser Thr Leu
            355                 360                 365

Phe Arg Trp Gln Ser Pro Cys Met Ile Pro Gly Ser Ala Ser Ser Gly
            370                 375                 380

Leu Arg Glu Ser Ser Gln Ser Ala Ser Thr Cys Thr Asp Gly Asn Asp
385                 390                 395                 400

Ser Gly Ala Gly Ser Ile Thr Gln Val Gly Arg Pro Ala Val Leu Phe
                405                 410                 415

Ala Pro Glu Gln Arg Cys Arg Arg Ala Asp Gln Arg Ser Cys Arg
            420                 425                 430

Gln Ile His Pro Gly Gly Gly Arg His Val Gln Ile Val Ala Ser Ala
            435                 440                 445

Arg Gly Thr Val Glu Ile Gly Ser Ile Ala Arg Leu Cys Gly Lys Asp
            450                 455                 460

Glu Ala Val Ala Ala Leu His Tyr Val Ala Pro Val Gly Glu Lys Gln
465                 470                 475                 480

Asp Tyr Ile Asp Arg Ala Leu Arg Asn Ile Gly Pro Tyr Leu Pro Ala
                485                 490                 495

Glu Val Pro Ala Leu Val Gly Ser Ile Ala Ala Thr Gly Pro Val Pro
            500                 505                 510

Gly Thr Ala Trp Ile Val Arg Gln Tyr Pro Lys Leu Leu Arg Ala Lys
            515                 520                 525

Ala Asn Trp Glu Asp Thr Trp Thr Phe Pro Ser Ile Glu Glu Lys His
            530                 535                 540

Arg Pro Arg Gly Ser Val Ala Gly Pro Val Phe Arg Val Asn Leu Gly
545                 550                 555                 560

Arg Ala Ile Pro Ser Arg Ala Ala Arg Ala Ala Glu Ile His Gly Ser
                565                 570                 575

His His His His His His
            580
```

```
<210> SEQ ID NO 80
<211> LENGTH: 582
<212> TYPE: PRT
<213> ORGANISM: Artificial Sequence
<220> FEATURE:
<223> OTHER INFORMATION: Made in a lab

<400> SEQUENCE: 80

Met Ala Thr Gly Ser Arg Thr Ser Leu Leu Ala Phe Gly Leu Leu
  1               5                  10                  15

Cys Leu Pro Trp Leu Gln Glu Gly Ser Ala Phe Pro Thr Ile Pro Gly
             20                  25                  30

Ser Ile Tyr Ser Thr Phe Ala Asp Arg Ala Tyr Pro Gly Gly Leu Thr
             35                  40                  45

Tyr Ser Gly His Pro Leu Ala Thr Ala Cys Ala Val Ala Thr Ile Asn
 50                  55                  60

Ala Met Glu Asp Glu Gly Met Val Ala Asn Ala Ala Arg Ile Gly Glu
 65                  70                  75                  80

Gln Val Leu Gly Pro Gly Leu Arg Asp Leu Ala Ala Arg His Arg Ser
                 85                  90                  95

Val Gly Glu Val Arg Gly Leu Gly Val Phe Trp Ala Gly Ser Ile Ser
            100                 105                 110

Ser Ala Leu Val Ala Ser Pro Pro Arg Ala Ala Ser Ser Ala Pro Ala
            115                 120                 125

Ser Ile Gly Leu Gly Pro Ser Gly Gln His Thr Ser Ile His Pro Arg
            130                 135                 140

Ser Ser Asn Gly Ser Pro Thr Val His Ile Ser Gln Ser Met Asn Ala
145                 150                 155                 160

Ala Ser Ser Gly Thr Ser Arg Arg Ser Ser Thr Leu Phe Arg Trp Gln
                165                 170                 175

Ser Pro Cys Met Ile Pro Gly Ser Ala Ser Ser Gly Leu Arg Glu Ser
                180                 185                 190

Ser Gln Ser Ala Ser Thr Cys Thr Asp Gly Asn Asp Ser Gly Ala Gly
            195                 200                 205

Ser Asp Arg Gln Ala Ser Arg Thr Val Ser Gly Val Pro Val Glu Ser
210                 215                 220

Asn Val Leu Ser Ala Gly Ile Arg Cys Arg Thr Pro Thr Arg Ala
225                 230                 235                 240

Val Ala Ile Cys Leu Ala Thr Leu Ala Ser Arg Gly Val Val Ala Pro
                245                 250                 255

Gln Pro Ala Gly Asp Val Ala Arg Ala Ala Ala Gly Ser Pro Trp
            260                 265                 270

Pro Val Arg Ser Val Ala Arg Pro Val Ala Val Leu Arg Thr Gly Pro
            275                 280                 285

Pro Pro Arg Arg Pro Ser Asp Thr Gly Ser Asp Gln Leu Gly Glu Pro
            290                 295                 300

Gly Ala Gln Gln Arg Gln Arg Gly Lys His Arg Asp Arg Arg Asp Val
305                 310                 315                 320

Pro Ala Gln Gln Arg Pro Ala Val His Pro Ala Gly Pro Gly Pro Ala
                325                 330                 335

Asp Arg Val Gly Val Asp Pro Gly Arg His Arg Arg Ala Arg Gly Gln
            340                 345                 350

His Gln Pro Arg Asp Gly Ser Ile Thr Gln Val Gly Arg Pro Ala Val
            355                 360                 365
```

```
Leu Phe Ala Pro Glu Gln Arg Cys Arg Arg Ala Asp Gln Arg Ser
    370                 375                 380

Cys Arg Gln Ile His Pro Gly Gly Arg His Val Gln Ile Val Ala
385                 390                 395                 400

Ser Ala Arg Gly Thr Val Glu Ile Gly Ser Ile Ala Arg Leu Cys Gly
                405                 410                 415

Lys Asp Glu Ala Val Ala Ala Leu His Tyr Val Ala Pro Val Gly Glu
                420                 425                 430

Lys Gln Asp Tyr Ile Asp Arg Ala Leu Arg Asn Ile Gly Pro Tyr Leu
                435                 440                 445

Pro Ala Glu Val Pro Ala Leu Val Gly Ser Asp Pro Glu Arg Ala Gly
                450                 455                 460

Leu Arg Val Glu Val Leu Gly Ala Gln Cys Arg Arg Arg Asp Val Val
465                 470                 475                 480

Gly Ala Gly Asp Ala Ala Val Gly Val Leu Gly Pro Gln Arg Gln
                485                 490                 495

His Arg Ala Arg Ala Asp Gly Ser Ile Ala Ala Thr Gly Pro Val Pro
                500                 505                 510

Gly Thr Ala Trp Ile Val Arg Gln Tyr Pro Lys Leu Leu Arg Ala Lys
                515                 520                 525

Ala Asn Trp Glu Asp Thr Trp Thr Phe Pro Ser Ile Glu Glu Lys His
                530                 535                 540

Arg Pro Arg Gly Ser Val Ala Gly Pro Val Phe Arg Val Asn Leu Gly
545                 550                 555                 560

Arg Ala Ile Pro Ser Arg Ala Arg Ala Ala Glu Ile His Gly Ser
                565                 570                 575

His His His His His His
            580

<210> SEQ ID NO 81
<211> LENGTH: 582
<212> TYPE: PRT
<213> ORGANISM: Artificial Sequence
<220> FEATURE:
<223> OTHER INFORMATION: Made in a lab

<400> SEQUENCE: 81

Met Ala Thr Gly Ser Arg Thr Ser Leu Leu Ala Phe Gly Leu Leu
1               5                   10                  15

Cys Leu Pro Trp Leu Gln Glu Gly Ser Ala Phe Pro Thr Ile Pro Gly
                20                  25                  30

Ser Ile Tyr Ser Thr Phe Ala Asp Arg Ala Tyr Pro Gly Gly Leu Thr
                35                  40                  45

Tyr Ser Gly His Pro Leu Ala Thr Ala Cys Ala Val Ala Thr Ile Asn
                50                  55                  60

Ala Met Glu Asp Glu Gly Met Val Ala Asn Ala Arg Ile Gly Glu
65                  70                  75                  80

Gln Val Leu Gly Pro Gly Leu Arg Asp Leu Ala Arg His Arg Ser
                85                  90                  95

Val Gly Glu Val Arg Gly Leu Gly Val Phe Trp Ala Gly Ser Asp Pro
                100                 105                 110

Glu Arg Ala Gly Leu Arg Val Glu Val Leu Gly Ala Gln Cys Arg Arg
                115                 120                 125

Arg Asp Val Val Gly Ala Gly Asp Ala Ala Val Gly Val Leu Gly
130                 135                 140
```

-continued

```
Pro Gln Arg Gln His Arg Ala Arg Ala Asp Gly Ser Ile Ser Ser Ala
145                 150                 155                 160

Leu Val Ala Ser Pro Pro Arg Ala Ala Ser Ala Pro Ala Ser Ile
            165                 170                 175

Gly Leu Gly Pro Ser Gly Gln His Thr Ser Ile His Pro Arg Ser Ser
            180                 185                 190

Asn Gly Ser Pro Thr Val His Ile Ser Gln Ser Met Asn Ala Ala Ser
            195                 200                 205

Ser Gly Thr Ser Arg Arg Ser Ser Thr Leu Phe Arg Trp Gln Ser Pro
            210                 215                 220

Cys Met Ile Pro Gly Ser Ala Ser Ser Gly Leu Arg Glu Ser Ser Gln
225                 230                 235                 240

Ser Ala Ser Thr Cys Thr Asp Gly Asn Asp Ser Gly Ala Gly Ser Asp
                245                 250                 255

Gln Leu Gly Glu Pro Gly Ala Gln Gln Arg Gln Arg Gly Lys His Arg
                260                 265                 270

Asp Arg Arg Asp Val Pro Ala Gln Gln Arg Pro Ala Val His Pro Ala
            275                 280                 285

Gly Pro Gly Pro Ala Asp Arg Val Gly Val Asp Pro Gly Arg His Arg
            290                 295                 300

Arg Ala Arg Gly Gln His Gln Pro Arg Asp Gly Ser Asp Arg Gln Ala
305                 310                 315                 320

Ser Arg Thr Val Ser Gly Val Pro Val Glu Ser Asn Val Leu Ser Ala
                325                 330                 335

Gly Ile Arg Cys Arg Thr Pro Thr Thr Arg Ala Val Ala Ile Cys Leu
                340                 345                 350

Ala Thr Leu Ala Ser Arg Gly Val Val Ala Pro Gln Pro Ala Gly Asp
            355                 360                 365

Val Ala Arg Ala Ala Ala Ala Gly Ser Pro Trp Pro Val Arg Ser Val
            370                 375                 380

Ala Arg Pro Val Ala Val Leu Arg Thr Gly Pro Pro Arg Arg Pro
385                 390                 395                 400

Ser Asp Thr Gly Ser Ile Thr Gln Val Gly Arg Pro Ala Val Leu Phe
                405                 410                 415

Ala Pro Glu Gln Arg Cys Arg Arg Ala Asp Gln Arg Ser Cys Arg
                420                 425                 430

Gln Ile His Pro Gly Gly Arg His Val Gln Ile Val Ala Ser Ala
                435                 440                 445

Arg Gly Thr Val Glu Ile Gly Ser Ile Ala Arg Leu Cys Gly Lys Asp
            450                 455                 460

Glu Ala Val Ala Ala Leu His Tyr Val Ala Pro Val Gly Glu Lys Gln
465                 470                 475                 480

Asp Tyr Ile Asp Arg Ala Leu Arg Asn Ile Gly Pro Tyr Leu Pro Ala
                485                 490                 495

Glu Val Pro Ala Leu Val Gly Ser Ile Ala Thr Gly Pro Val Pro
            500                 505                 510

Gly Thr Ala Trp Ile Val Arg Gln Tyr Pro Lys Leu Leu Arg Ala Lys
            515                 520                 525

Ala Asn Trp Glu Asp Thr Trp Thr Phe Pro Ser Ile Glu Glu Lys His
            530                 535                 540

Arg Pro Arg Gly Ser Val Ala Gly Pro Val Phe Arg Val Asn Leu Gly
545                 550                 555                 560
```

```
Arg Ala Ile Pro Ser Arg Ala Ala Arg Ala Ala Glu Ile His Gly Ser
                565             570                 575
His His His His His His
            580
```

COMPOUNDS FOR TREATMENT OF INFECTIOUS AND IMMUNE SYSTEM DISORDERS AND METHODS FOR THEIR USE

TECHNICAL FIELD

The present invention relates generally to the detection, treatment and prevention of infectious diseases. In particular, the invention is related to compounds comprising immunogenic epitopes isolated from *Mycobacterium vaccae*, and the use of such compounds in vaccination or immunotherapy against infectious disease, including mycobacterial infections such as infection with *Mycobacterium tuberculosis* or *Mycobacterium avium*, and in certain treatments for immune disorders and cancer.

BACKGROUND OF THE INVENTION

The present invention relates generally to the treatment and prevention of infectious diseases, and to the treatment of certain immune disorders and cancers. In particular, the invention is related to compounds and methods for the treatment and prevention of mycobacterial infections including infection with *Mycobacterium tuberculosis* or *Mycobacterium avium*.

Tuberculosis is a chronic, infectious disease that is caused by infection with *Mycobacterium tuberculosis* (*M. tuberculosis*). It is a major disease in developing countries, as well as an increasing problem in developed areas of the world, with about 8 million new cases and 3 million deaths each year. Although the infection may be asymptomatic for a considerable period of time, the disease is most commonly manifested as a chronic inflammation of the lungs, resulting in fever and respiratory symptoms. If left untreated, significant morbidity and death may result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behaviour is difficult to monitor. Some patients do not complete the course of treatment, which can lead to ineffective treatment and the development of drug resistant mycobacteria.

Inhibiting the spread of tuberculosis requires effective vaccination and accurate, early diagnosis of the disease. Currently, vaccination with live bacteria is the most efficient method for inducing protective immunity. The most common mycobacterium employed for this purpose is Bacillus Calmette-Guerin (BCG), an a virulent strain of *Mycobacterium bovis*. However, the safety and efficacy of BCG is a source of controversy and some countries, such as the United States of America, do not vaccinate the general public. Diagnosis of *M. tuberculosis* infection is commonly achieved using a skin test, which involves intradermal exposure to tuberculin PPD (protein-purified derivative). Antigen-specific T cell responses result in measurable induration at the injection site by 48–72 hours after injection, thereby indicating exposure to mycobacterial antigens. Sensitivity and specificity have, however, been a problem with this test, and individuals vaccinated with BCG cannot be distinguished from infected individuals.

A less well-known mycobacterium that has been used for immunotherapy for tuberculosis, and also leprosy, is *Mycobacterium vaccae*, which is non-pathogenic in humans. However, there is less information on the efficacy of *M. vaccae* compared with BCG, and it has not been used widely to vaccinate the general public. *M. bovis* BCG and *M. vaccae* are believed to contain antigenic compounds that are recognised by the immune system of individuals exposed to infection with *M. tuberculosis*.

Several patents and other publications disclose treatment of various conditions by administering mycobacteria, including *M. vaccae*, or certain mycobacterial fractions. International Patent Publication WO 91/02542 discloses treatment of chronic inflammatory disorders in which a patient demonstrates an abnormally high release of IL-6 and/or TNF or in which the patient's IgG shows an abnormally high proportion of agalactosyl IgG. Among the disorders mentioned in this publication are psoriasis, rheumatoid arthritis, mycobacterial disease, Crohn's disease, primary biliary cirrhosis, sarcoidosis, ulcerative colitis, systemic lupus erythematosus, multiple sclerosis, Guillain-Barre syndrome, primary diabetes mellitus, and some aspects of graft rejection. The therapeutic agent preferably comprises autoclaved *M. vaccae* administered by injection in a single dose.

U.S. Pat. No. 4,716,038 discloses diagnosis of, vaccination against and treatment of autoimmune diseases of various types, including arthritic diseases, by administering mycobacteria, including *M. vaccae*. U.S. Pat. No. 4,724,144 discloses an immunotherapeutic agent comprising antigenic material derived from *M. vaccae* for treatment of mycobacterial diseases, especially tuberculosis and leprosy, and as an adjuvant to chemotherapy. International Patent Publication WO 91/01751 discloses the use of antigenic and/or immunoregulatory material from *M. vaccae* as an immunoprophylactic to delay and/or prevent the onset of AIDS. International Patent Publication WO 94/06466 discloses the use of antigenic and/or immunoregulatory material derived from *M. vaccae* for therapy of HIV infection, with or without AIDS and with or without associated tuberculosis.

Traditional vaccines contain the disease-causing organism (or a component thereof) in either attenuated or killed form. As an alternative approach to traditional vaccines, DNA vaccines have been developed for diseases as diverse as AIDS, influenza, cancer and malaria. Clinical trials of DNA vaccines are in progress for a number of these diseases. A typical DNA vaccine consists of DNA encoding an antigen cloned in a non-active plasmid carrier. Expression of the antigen encoded by the vaccine DNA is usually under control of a strong promoter, such as human β-actin, Rous sarcoma virus (RSV) or CMV promoter (Ramsay A J, Ramshaw I A, and Ada G L. *Immunology and Cell Biology* 75:360–363, 1997). The first experimental evidence that DNA vaccines were able to induce the desired immune response was produced by Tang et al. (Tang D-C, Devit M, Johnston S A. *Nature* 356:152–154, 1992). In these experiments, mice inoculated with plasmids containing the gene encoding for human growth hormone developed specific primary antibody responses.

Immune responses to two DNA vaccines containing genes from *M. tuberculosis* have been evaluated in animal models. The first vaccine contained the gene coding for the GroEL stress protein (65 kDa protein) (Tascon R E, Colston M J, Ragno S, Stavropoulos E, Gregory D, Lowrie D B. *Nature Med.* 2:888–892, 1996). Mice injected with this DNA vaccine were protected at a level equivalent to mice receiving the traditional BCG vaccine. The second DNA vaccine against *M. tuberculosis* contained DNA encoding an antigen from the antigen 85 complex and similar results to the study by Tang et al. were obtained (Huygen K, Content J, Denis O, Montgomery D L, Yawman A M, Deck R R, DeWitt C M, Orm I A, Baldwin S, D'Souza C, Drowart A, Lozes E, VandenBussche P, Van Vooren J -P, Liu M A and Ulmer J B. *Nature Med.* 2:893–898, 1996). U.S. Pat. No. 5,736,524 discloses vaccination of domestic mammals or livestock against infection by *M. tuberculosis* or *M. bovis* by administering a polynucleotide tuberculosis vaccine comprising the *M. tuberculosis* antigen 85 gene operably linked to transcription regulatory elements.

The first human DNA vaccine trial was reported recently (Wang R, Doolan D L, Le T P, Hedstrom R C, Coonan K M, Charoenvit Y, Jones T R, Hobart P, Margalith M, Ng J, Weiss W R, Sedegah M, de Taisne C, Norman J A, Hoffman S L. *Science* 282:476–80, 1998). In this trial, an antigen from *Plasmodium falciparum*, the causative agent of malaria, was injected into healthy volunteers. The desired immune response was elicited, as demonstrated by the presence of cytotoxic T ($CD8^+$) lymphocytes (CTL), suggesting that the immune system would be able to clear parasites from infected patients. Safety and immunogenicity of a human DNA vaccine against HIV-1 infection was determined in a trial performed by McGregor et al. (MacGregor R R, Boyer J D, Ugen K E, Lacy K E, Gluckman S J, Bagarazzi M L, Chattergoon M A, Baine Y, Higgins T J, Ciccarelli R B, Coney L R, Ginsberg R S, Weiner D B. *J. Infect. Dis.* 178:92–100, 1998). Experimental data from other DNA vaccine experiments has also suggested that antibodies, MHC class 1-restricted $CD8^+$ CTL and class II-restricted $CD4^+$ helper T cells are produced following injection with DNA vaccines (Ramsay, A J, Ramshaw, I A and Ada, G L. *Immunology and Cell Biology* 75:360–363, 1997).

DNA vaccines have distinct advantages over more traditional vaccines containing killed or attenuated organisms. DNA vaccination induces immune responses that are long-lived and therefore only a single inoculation may be required. DNA encoding a number of antigens may be incorporated into a single plasmid thereby providing protection against a number of diseases. The technology for DNA vaccine production is relatively simple and the same technology can be used to produce all vaccines, with a resulting cheaper production cost. Delivery of efficacious traditional vaccines to the patient are dependent on maintaining an unbroken "cold chain" from manufacturer to clinic. DNA vaccines produced in solution or in dried form are not sensitive to storage conditions.

One limitation of DNA vaccines is that the immune response is induced against protein components of the pathogen, only. Some traditional vaccines are aimed at inducing an immune response against the polysaccharide outer membrane of pathogens, for example the pneumococcal vaccine against bacterial pneumonia. These molecules are not yet targeted by DNA vaccines.

Recently, alternative ways of constructing and applying DNA vaccines have been developed. In one of the techniques, called Somatic Transgene Immunisation (STI), the plasmid DNA carrying an immunoglobulin heavy chain gene under the control of tissue-specific regulatory elements was inoculated directly into the spleen of mice, with subsequent expression of the antigen on the surface of B-cells (Xiong S, Gerloni M, Zanetti M. *Proc. Natl. Acad. Sci. USA* 94:6352–6357, 1997). These B cells produced antibodies against the expressed antigen, leading to an immune response. Subsequent studies showed that STI induced persistent immunologic memory for up to 2 years (Gerloni M, Xiong S, Zanetti M. *Vaccine* (2–3):293–297, 1998).

Expression Library Immunization (ELI) is another technique employing DNA vaccines (Barry M A, Lai W C and Johnston, S A. *Nature* 377:632–635, 1995). In this technique, fragments of the complete genome of a pathogen are cloned into a vector and used as vaccine. Selection of protective antigen(s), particularly those inducing CTL, is done by screening and re-screening pools of clones until single clones can be identified. The polynucleotide or polypeptide identified may then be incorporated into a proven delivery system.

Progress on the development of an epitope-based vaccine for the treatment and prevention of HIV infection by scientists at Epimmune Inc. (San Diego, Calif.), has been published recently (Ishioka G Y, et al. *Journal of Immunology* 162:3915–3925, 1999).

There remains a need in the art for effective compounds and methods for preventing and treating infectious disorders, such as tuberculosis and other mycobacterial infections in humans and in domestic mammals or livestock, and for the treatment of certain immune system-related disorders.

SUMMARY OF THE INVENTION

Briefly stated, the present invention provides compounds and methods for the prevention and treatment of infectious diseases, such as mycobacterial infections, and for the treatment of immune disorders and cancers.

In a first aspect, isolated polynucleotides are provided that are derived front the *M. vaccae* genome. These polynucleotides encode polypeptide epitopes selected on the basis of their immunogenic properties as illustrated by results from a number of immunological assays. In specific embodiments, the inventive polynucleotides comprise a sequence selected from the group consisting of: (a) sequences provided in SEQ ID NO: 8–21; (b) sequences having at least 50%, 75% or 90% identical residues to a sequence of SEQ ID NO: 8–21 as determined using the computer algorithm BLASTN; and (c) compliments of the sequences of (a) and (b).

In a second aspect, the invention provides isolated polypeptides comprising an immunogenic epitope of a *M. vaccae* antigen. In specific embodiments, the inventive polypeptides comprise a sequence selected from the group consisting of: (a) sequences provided in SEQ ID NO: 61–77; and (b) sequences having at least 50%, 75% or 90% identical residues to a sequence of SEQ ID NO: 61–77 as determined using the computer algorithm FASTX.

DNA constructs comprising at least one of the inventive polynucleotides, and host cells transformed or transfected with such DNA constructs are also provided.

In another aspect, the present invention provides fusion proteins comprising at least one polypeptide of the present invention.

Within other aspects, the present invention provides pharmaceutical compositions that comprise at least one of the inventive polypeptides, polynucleotides, fusion proteins or DNA constructs, and a physiologically acceptable carrier The invention also provides vaccines comprising at least one of the above polypeptides, polynucleotides, fusion proteins or DNA constructs and a non-specific immune response amplifier.

In yet another aspect, methods are provided for enhancing an immune response in a patient, comprising administering to a patient an effective amount of one or more of the above pharmaceutical compositions and/or vaccines. In one embodiment, the immune response is a Th1 response.

In further aspects of this invention, methods are provided for the treatment of a disorder in a patient, comprising administering to the patient a pharmaceutical composition or vaccine of the present invention. In certain embodiments, the disorder is selected from the group consisting of immune disorders, infectious diseases and cancer.

These and other aspects of the present invention will become apparent upon reference to the following detailed description. All references disclosed herein are hereby incorporated by reference in their entirety as if each was incorporated individually.

DETAILED DESCRIPTION OF THE INVENTION

As noted above, the present invention is generally directed to compositions and methods for preventing and treating disorders including infectious diseases and certain immune disorders and cancers. Examples of such disorders include, but are not limited to, mycobacterial infections, including M. tuberculosis and M. avium infections; and disorders in which the stimulation of a Th1 immune response is beneficial, including (but not limited to) psoriasis, allergic rhinitis.

Considerable research efforts have been directed towards elucidating the mechanism of immune response to mycobacterial infection, in particular M. tuberculosis infection. While macrophages have been shown to act as the principal effectors of M. tuberculosis immunity, T cells are the predominant inducers of such immunity. The essential role of T cells in protection against M. tuberculosis infection is illustrated by the frequent occurrence of M. tuberculosis in AIDS patients, due to the depletion of CD4 T cells associated with human immunodeficiency virus (HIV) infection. Mycobacterium-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit M. tuberculosis infection. Furthermore, it is known that IFN-γ stimulates human macrophages to make 1,25-dihydroxy-vitamin D3. Similarly, IL-12 has been shown to play a role in stimulating resistance to M. tuberculosis infection. Another property of CD4$^+$ T cells and macrophages is their ability to activate CD8$^+$ cytotoxic T cells that are capable of killing pathogen-infected cells. CD8$^+$ T cells have been shown to kill macrophages and other cells that harbour M. tuberculosis. For a review of the immunology of M. tuberculosis infection, see Chan and Kaufmann in Bloom, ed. *Tuberculosis: pathogenesis, protection and control*, ASM Press: Washington, D.C., 1994.

In one aspect, the compositions of the present invention include polypeptides that comprise at least one immunogenic epitope of a M. vaccae antigen, or a variant thereof. In specific embodiments, the inventive polypeptides comprise a sequence provided in SEQ ID NOS: 61–77. Such polypeptides stimulate T cell proliferation, and/or interferon gamma secretion from T cells of individuals exposed to M. tuberculosis. As used herein, the term "polypeptide" encompasses amino acid chains of any length, including full-length proteins (i.e., antigens), wherein the amino acid residues are linked by covalent peptide bonds. Thus, a polypeptide comprising an immunogenic epitope of one of the above antigens may consist entirely of the immunogenic epitope, or may contain additional sequences. The additional sequences may be derived from the native M. vaccae antigen or may be heterologous, and such sequences may (but need not) be immunogenic.

"Immunogenic," as used herein, refers to the ability to elicit an immune response in a patient, such as a human, or in a biological sample. In particular, an immunogenic epitope is that portion of a polypeptide that is capable of stimulating cell proliferation, interleukin-12 production or interferon-γ production in biological samples comprising one or more cells selected from the group of T cells, NK cells, B cells and macrophages, where the cells are derived from a mycobacteria-immune individual. In general, an immunogenic epitope will stimulate proliferation of PBMC from mycobacteria-immune individuals at levels at least two-fold greater than that observed in control PBMC, determined using assay techniques detailed below in Example 1. Alternatively, or additionally, an immunogenic epitope will stimulate the production of interferon-γ in PBMC from mycobacteria-immune individuals at levels that are at least two-fold greater than those observed in control cells as determined by at least a two-fold increase in OD in an ELISA assay as detailed in Example 1. A mycobacteria-immune individual is one who is considered to be resistant to the development of mycobacterial infection by virtue of having mounted an effective T cell response to M. tuberculosis or to environmental saprophytes or to BCG. Such individuals may be identified based on a strongly positive (i.e., greater than about 10 mm diameter induration) intradermal skin test response to tuberculosis proteins (PPD), and an absence of any symptoms of tuberculosis infection. Polypeptides comprising at least an immunogenic epitope of one or more M. vaccae antigens may generally be used to induce protective immunity against tuberculosis in a patient and/or to stimulate an immune response in a patient.

In another aspect, the compositions of the present invention comprise isolated polynucleotides that encode an immunogenic epitope of a M. vaccae antigen. In specific embodiments, the inventive polynucleotides comprise a sequence of SEQ ID NOS: 5–21. Complements of the inventive isolated polynucleotides, reverse complements of such isolated polynucleotides and reverse sequences of such isolated polynucleotides are also provided, together with variants of such sequences. The present invention also encompasses polynucleotide sequences that differ from the disclosed sequences but which, due to the degeneracy of the genetic code, encode a polypeptide which is the same as that encoded by a polynucleotide sequence disclosed herein.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and/or DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments. Anti-sense polynucleotides and techniques involving anti-sense polynucleotides are well known in the art and are described, for example, in Robinson-Benion et al. "Antisense techniques," *Methods in Enzymol.* 254:363–375, 1995; and Kawasaki et al. *Artific. Organs* 20:836–848, 1996.

The definition of the terms "complement", "reverse complement" and "reverse sequence", as used herein, is best illustrated by the following example. For the sequence 5' AGGACC 3', the complement, reverse complement and reverse sequence are as follows:

| complement | 3' TCCTGG 5' |
|---|---|
| reverse complement | 3' GGTCCT 5' |
| reverse sequence | 5' CCAGGA 3'. |

All of the polynucleotides and polypeptides described herein are isolated and purified, as those terms are commonly used in the art.

The compositions and methods of this invention also encompass variants of the above polypeptides and polynucleotides. Variants may be naturally occurring allelic variants, or non-naturally occurring variants. As used herein, the term "variant" covers any sequence which has at least about 40%, more preferably at least about 60%, more preferably yet at least about 75% and most preferably at least about 90% identical residues (either nucleotides or amino acids) to a sequence of the present invention. The percentage of identical residues is determined by aligning the two sequences to be compared, determining the number of identical residues in the aligned portion, dividing that number by the total length of the inventive, or queried, sequence and multiplying the result by 100.

Polynucleotide or polypeptide sequences may be aligned, and percentage of identical nucleotides in a specified region may be determined against another polynucleotide, using computer algorithms that are publicly available. Two exemplary algorithms for aligning and identifying the similarity of polynucleotide sequences are the BLASTN and FASTA algorithms. The similarity of polypeptide sequences may be examined using the BLASTP and FASTX algorithms. Both the BLASTN and BLASTP software are available on the NCBI anonymous FTP server. The BLASTN algorithm Version 2.0.6 [Sep. 16, 1998], set to the default parameters described in the documentation and distributed with the algorithm, is preferred for use in the determination of variants according to the present invention. The use of the BLAST family of algorithms, including BLASTN and BLASTP, is described at NCBI's website at URL and in the publication of Altschul, Stephen F, et al. "Gapped BLAST and PSI-BLAST: a new generation of protein database search programs," *Nucleic Acids Res.* 25:3389–3402, 1997. The computer algorithm FASTA is available on the Internet. Version 3.1t11 August 1998, of the FASTA and FASTX algorithms, set to the default parameters described in the documentation and distributed with the algorithms, are preferred for use in the determination of variants according to the present invention. The use of the FASTA algorithm is described in Pearson W R and Lipman D J. *Proc. Natl. Acad. Sci. USA* 85:2444–2448, 1988; and Pearson W R. *Methods in Enzymology* 183:63–98, 1990. The use of the FASTX algorithm is described, for example, in Pearson W R, et al., *Genomics* 46:24–36, 1997.

The following running parameters are preferred for determination of alignments and similarities using BLASTN that contribute to the E values and percentage identity: Unix running command: blastall -p blastn -d embldb -e 10 -G 0 -E 0 -r 1 -v 30 -b 30 -i queryseq -o results; and parameter default values: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (blastn only) [Integer]; -v Number of one-line descriptions (V) [Integer]; -b Number of alignments to show (B) [Integer]; -i Query File [File In]; -o BLAST report Output File [File Out] Optional. For BLASTP the following running parameters are preferred: blastall -p blastp -d swissprotdb -e 10 -G 0 -E 0 -v 30 -b 30 -i queryseq -o results; -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

For determination of alignments and similarities using FASTX, the following UNIX command is preferred: fastx -E 10 -b 30 -H queryseq>output, while for FASTA, the following UNIX command is preferred: fasta -E 2 -b 30 -H -n queryseq>output.

The "hits" to one or more database sequences by a queried sequence produced by BLASTN, BLASTP, FASTA, FASTX or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the default parameters. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at the default parameters.

Variant polynucleotide sequences will generally hybridize to the recited polynucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

A polypeptide of the present invention may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

As used herein, the term "x-mer," with reference to a specific value of "x," refers to a polynucleotide comprising at least a specified number ("x") of contiguous residues of any of the polynucleotides identified as SEQ ID NOS: 5–21. The value of x may be from about 20 to about 600, depending upon the specific sequence.

Polynucleotides of the present invention comprehend polynucleotides comprising at least a specified number of contiguous residues (x-mers) of any of the polynucleotides identified as SEQ ID NO: 5–21 or their variants. According to preferred embodiments, the value of x is preferably at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide identified as SEQ ID NO: 5–21 or a variant of one of the polynucleotides identified as SEQ ID NOS: 5–21.

In general, the inventive polypeptides and polynucleotides, may be prepared using any of a variety of procedures. For example, polypeptides may be produced recombinantly by inserting a polynucleotide that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are E. coli, mycobacteria, insect, yeast or a mammalian cell line such as COS or CHO. The polynucleotides expressed in this manner may encode naturally occurring antigens, portions of naturally occurring antigens, or other variants thereof.

Polynucleotides of the present invention may be isolated by screening a M. vaccae genomic DNA library as described below in Example 1. Alternatively, polynucleotides encoding M. vaccae epitopes may be obtained by screening an appropriate M. vaccae cDNA or genomic DNA library for DNA sequences that hybridize to degenerate oligonucleotides derived from amino acid sequences of isolated epitopes. Suitable degenerate oligonucleotides may be designed and synthesized, and the screen may be performed as described, for example in Sambrook et al. *Molecular cloning: a laboratory manual.* CSHL Press: Cold Spring Harbor, N.Y., 1989. Polymerase chain reaction (PCR) may be employed to isolate a nucleic acid probe from genomic DNA, or a cDNA or genomic DNA library, using techniques well known in the art; The library screen may then be performed using the isolated probe.

Regardless of the method of preparation, the epitopes described herein have the ability to induce an immunogenic response. More specifically, as discussed above, the epitopes have the ability to induce cell proliferation and/or cytokine production (for example, interferon-γ and/or interleukin-12 production) in T cells, NK cells, B cells or macrophages derived from a mycobacteria-immune individual.

The selection of cell type for use in evaluating an immunogenic response to an epitope will depend on the desired response. For example, interleukin-12 production is most readily evaluated using preparations containing T cells, NK cells, B cells and/or macrophages derived from mycobacteria-immune individuals may be prepared using methods well known in the art. For example, a preparation of peripheral blood mononuclear cells (PBMCs) may be employed without further separation of component cells. PBMCs may be prepared, for example, using density centrifugation through Ficoll™ (Winthrop Laboratories, N.Y.). T cells for use in the assays described herein may be purified directly from PBMCs. Alternatively, an enriched T cell line reactive against mycobacterial proteins, or T cell clones reactive to individual mycobacterial proteins, may be employed. Such T cell clones may be generated by, for example, culturing PBMCs from mycobacteria-immune individuals with mycobacterial proteins for a period of 2–4 weeks. This allows expansion of only the mycobacterial protein-specific T cells, resulting in a line composed solely of such cells. These cells may then be cloned and tested with individual proteins, using methods well known in the art, to more accurately define individual T cell specificity. Assays for cell proliferation or cytokine production in T cells, NK cells, B cells or macrophages may be performed, for example, using the procedures described below.

Among the immunogenic epitopes, polypeptides and/or polynucleotides of the present invention, those having superior therapeutic properties may be distinguished based on the magnitude of the responses in the above assays and based on the percentage of individuals for which a response is observed. In addition, epitopes having superior therapeutic properties will not stimulate cell proliferation or cytokine production in vitro in cells derived from more than about 25% of individuals that are not mycobacteria-immune, thereby eliminating responses that are not specifically due to mycobacteria-responsive cells. Thus, those antigens that induce a response in a high percentage of T cell, NK cell, B cell or macrophage preparations from mycobacteria-immune individuals (with a low incidence of responses in cell preparations from other individuals) have superior therapeutic properties.

Epitopes with superior therapeutic properties may also be identified based on their ability to diminish the severity of M. tuberculosis infection, or other mycobacterial infection, in experimental animals, when administered as a vaccine. Suitable vaccine preparations for use in experimental animals are described in detail below.

Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems, Inc. (Foster City, Calif.), and may be operated according to the manufacturer's instructions. Variants of a native epitope may be prepared using standard mutagenesis techniques, such as oligonucleotide-directed site-specific mutagenesis.

Sections of the DNA sequence may also be removed using standard techniques to permit preparation of truncated polypeptides.

The present invention also provides fusion proteins comprising a first and a second inventive polypeptide or, alternatively, a polypeptide of the present invention and a known *M tuberculosis* antigen, such as the 38 kDa antigen described in Andersen and Hansen, *Infect. Immun.* 57:2481–2488, 1989, together with variants of such fusion proteins. In a related aspect, DNA constructs comprising a first and a second inventive polynucleotide arc also provided. Preparation of a construct comprising multiple epitopes of the present invention and expression of the corresponding recombinant protein is detailed below in Example 4. In general, a poly-nucleotide encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide fold into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; and U.S. Pat. Nos. 4,935,233 and 4,751,180. The linker sequence may be from 1 to about 50 amino acids in length. Peptide linker sequences are not required when the first and second polypeptides have non-essential N-terminal amino acid regions that can be used to separate the functional domains and prevent steric interference. The ligated DNA sequences encoding the fusion proteins are cloned into suitable expression systems using techniques known to those of ordinary skill in the art.

In another aspect, the present invention provides methods for using one or more of the inventive polypeptides or fusion proteins (or polynucleotides encoding such polypeptides or fusion proteins) to induce protective immunity against disorders such as tuberculosis in a patient. As used herein, a "patient" refers to any warm-blooded animal, preferably a human. A patient may be afflicted with a disease, or may be free of detectable disease or infection. In other words, protective immunity may be induced to prevent or treat tuberculosis.

In related aspects, the *M. vaccae* polynucleotides and polypeptides of the present invention may be employed to activate T cells and NK cells; to stimulate the production of cytokines (in particular Th1 class of cytokines) in human PBMC; to produce anti-epitope antibodies; and/or to induce long-term memory cells.

For use in such methods, the polypeptide, fusion protein or polynucleotide is generally present within a pharmaceutical composition or a vaccine. Pharmaceutical compositions may comprise one or more polypeptides, each of which may contain one or more of the above sequences (or variants thereof, and a physiologically acceptable carrier. Vaccines may comprise one or more of the above polypeptides and a non-specific immune response amplifier, such as an adjuvant or a liposome, into which the polypeptide is incorporated. Such pharmaceutical compositions and vaccines may also contain other mycobacterial antigens, either, as discussed above, incorporated into a fusion protein or present within a separate polypeptide.

Alternatively, a vaccine of the present invention may contain a polynucleotide encoding one or more polypeptides as described above, such that the polypeptide is generated in situ. In such vaccines, the polynucleotide may be present within any of a variety of delivery systems known to those of ordinary skill in the art, including nucleic acid expression systems, bacterial and viral expression systems. Appropriate nucleic acid expression systems contain the necessary DNA/RNA sequences for expression in the patient (such as a suitable promoter and terminator signal). Bacterial delivery systems involve the administration of a bacterium (such as Bacillus Calmette-Guerin) that expresses an immunogenic epitope of the polypeptide on its cell surface. In a preferred embodiment, the DNA and/or RNA may be introduced using a viral expression system (e.g., vaccinia or other poxvirus, retrovirus, or adenovirus), that may involve the use of a non-pathogenic, or defective, replication competent virus. Techniques for incorporating DNA and/or RNA into such expression systems are well known in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells. Methods for the administration of polynucleotide sequences comprising DNA and/or RNA include those disclosed in U.S. Pat. Nos. 5,580,859 and 5,589,466.

A polynucleotide vaccine as described above may be administered simultaneously with or sequentially to either a polypeptide of the present invention or a known mycobacterial antigen, such as the 38 kDa antigen described above. For example, administration of DNA encoding a polypeptide of the present invention, may be followed by administration of an antigen in order to enhance the protective immune effect of the vaccine.

Routes and frequency of administration, as well as dosage, will vary from individual to individual and may parallel those currently being used in immunization using *M. bovis* BCG. In general, the pharmaceutical compositions and vaccines may be administered by injection (e.g., intradermal, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or polynucleotide that, when administered as described above, is capable of raising an immune response in a patient sufficient to protect the patient from mycobacterial infection for at least 1–2 years. In general, the amount of polypeptide present in a dose (or produced in situ by the polynucleotide in a dose) ranges from about 1 pg to about 100 mg per kg of host, typically from about 10 pg to about 1 mg, and preferably from about 100 μg to about 1 pg. Suitable dose sizes will vary with the size of the patient, but will typically range from about 0.1 ml to about 5 ml.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to non-specifically enhance the immune response. Most adjuvants contain a substance designed to protect the antigen from rapid catabolism, such as aluminum hydroxide or mineral oil, and a non-specific stimulator of immune responses, such as lipid A, *Bordetella pertussis, M. tuberculosis*, or, as discussed below, *M. vaccae*. Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A and Quil A.

The following examples are offered by way of illustration and not by way of limitation.

EXAMPLE 1

CLONING AND SELECTION OF IMMUNOGENIC *M. Vaccae* EPITOPES

*M. vaccae* (ATCC Number 15483, Rockville, Md.) was cultured in medium 90 (yeast extract, 2.5 g/l; tryptone, 5 g/l; glucose, 1 g/l) at 37° C. for four days. Genomic DNA was isolated from these cells following standard protocols and then digested with restriction endonuclease Sau3A under conditions that produced DNA fragments of approximately 0.25 kb. The fragments were purified using the QIAquick PCR clean-up system (Qiagen, Venlo, The Netherlands).

To express the cloned *M. vaccae* DNA in three different reading frames, the pcDNA3 expression vector (Invitrogen, Carlsbad, Calif.) was modified by insertion of a human growth hormone signal peptide (to facilitate recombinant protein secretion) amplified with three different 3' primers. These primers allowed the insertion of one or two extra base pairs into the PCR product to shift the reading frame of the expressed polypeptide. The primers were AD105 (human growth hormone 5' primer; SEQ ID NO: 1) and the three human growth hormone (hGH) 3' primers AD106, AD107 and AD108 (SEQ ID NOS: 2–4, respectively). From these PCR fragments, most of the hGH sequence downstream of the leader sequence cleavage site was removed by digestion with the restriction endonuclease BsgII. The hGH PCR fragments were then cloned into the pcDNA3 expression vector following digestion with the restriction endonucleases HindIII and BamHI. The nucleotide sequence of the inserted fragments are given in SEQ ID NOS: 5–7, with the corresponding amino acid sequences being provided in SEQ ID NOS: 61–63, respectively. Three expression libraries (one for each of the three reading frames) were constructed by cloning the 0.25 kb *M. vaccae* PCR fragments, prepared as described above, into the BamHI cloning site of the chimeric pcDNA3/human growth hormone vectors (pcDNA3-hGH1', pcDNA3-hGH2' and pcDNA3-hGH3'). Replica lift master plates were made of bacterial colonies transformed with the library constructs and stored. Plasmid DNA, prepared from these colonies, was divided into 500 pools, each containing DNA from 40 to 50 plasmids. The DNA was transfected into COS7 cells using lipofectamine (BRL Life Technologies, Gaithersburg Md.) and the immunogenic properties of the products of each group were determined by a spleen cell assay, wherein the production of IFN-γ in cultures of spleen cells obtained from mice primed with heat-killed *M. vaccae* was determined by ELISA as described below.

Plasmid pools that encoded recombinant polypeptides eliciting an immune response (as determined by the ability to increase IFN-γ production in the spleen cell assay), were subdivided into smaller pools containing 10 plasmids each and these pools were again transfected into COS7 cells. The culture supernatants of these cells were subjected to the spleen cell assay as described above.

After three rounds of screening, 120 plasmids were identified that encoded recombinant polypeptides stimulating spleen cells of heat-killed *M. vaccae*-immunised mice to produce IFN-γ. The 120 supernatants of COS7 cells transfected with these plasmids were screened in two additional assays, namely the mouse memory assay and the human peripheral blood mononuclear cell (PBMC) assay. In the mouse long-term memory assay, mice were injected with a sub-lethal dose of $10^4$ colony forming units (CFU) of *M. tuberculosis*. After 4 weeks, the mice were treated with antibiotics for a further 4 weeks to cure them of *M. tuberculosis* infection, followed by a resting period of 4 weeks. A second injection of live *M. tuberculosis* ($5 \times 10^5$ CFU) was given before the immunogenicity of the plasmid products was measured four days later using the spleen cell assay described above.

In the PBMC assay, the 120 supernatants of COS7 cells transfected with the plasmids were screened for the ability to induce T-cell proliferation and IFN-γ production in peripheral blood cells from mycobacteria-immune human donors. These donors were known to be PPD (purified protein derivative from *M. tuberculosis*) positive and their T cells were shown to proliferate and produce IFN-γ in response to PPD. Donor PBMCs and COS7 supernatants were cultured in medium comprising RPMI 1640 supplemented with 10% (v/v) autologous serum, penicillin (60 μg/ml), streptomycin (100 μg/ml), and glutamine (2 mM). After 3 days, 50 μl of medium was removed from each well for the determination of IFN-γ levels, as described below. The plates were cultured for a further 4 days and then pulsed with 1 μCi/well of tritiated thymidine for 18 hours, harvested and tritium uptake determined using a scintillation counter. Supernatants that stimulated proliferation in two replicates at levels two-fold greater than the proliferation observed in cells cultured in medium alone were considered positive.

IFN-γ was measured using an enzyme-linked immunosorbent assay (ELISA) as follows. ELISA plates were coated with a mouse monoclonal antibody directed to human IFN-γ (Endogen, Wobural, Mass.) by incubating the wells with 1 μg/ml antibody in phosphate-buffered saline (PBS) for 4 hours at 4° C. Wells were blocked with PBS containing 0.2% Tween 20 for 1 hour at room temperature. The plates were then washed four times in PBS/0.2% Tween 20, and samples diluted 1:2 in culture medium in the ELISA plates were incubated overnight at room temperature. The plates were again washed, and a biotinylated polyclonal rabbit anti-human IFN-γ serum (Endogen), diluted to 1 μg/ml in PBS, was added to each well. The plates were then incubated for 1 hour at room temperature, washed, and horseradish peroxidase-coupled avidin A (Vector Laboratories, Burlingame, Calif.) was added at a 1:4,000 dilution in PBS. After a further 1 hour incubation at room temperature, the plates were washed and orthophenylenediamine (OPD) substrate added. The reaction was stopped after 10 minutes with 10% (v/v) HCl. The optical density (OD) was determined at 490 nm. Supernatants that resulted in both replicates giving an OD two-fold greater than the mean OD from cells cultured in medium alone were considered positive.

From the results of these two assays, 59 plasmids were identified that encoded recombinant polypeptides containing immunogenic determinants, or epitopes. These epitopes were found to elicit an immune response in mice and humans and are cross-reactive with *M. tuberculosis* immunogenic determinants inducing long term responses. These plasmids were tested for their ability to induce protective immunity in the mouse model of tuberculosis as follows. Each plasmid (100 μg of DNA) was injected IM in the tibialis anterior of anaesthetised mice, three times every three weeks. After nine weeks, the mice were challenged with *M. tuberculosis* ($5\times10^5$ CFU). Organ homogenates from lungs and spleens were prepared in week 12 and plated out on 7H9 medium supplemented with oleic acid-albumin-dextrose-catalase (OADC) to determine the number of CFU present in each homogenate. Results were recorded after a two-week incubation period.

Using the protocols described above, eight plasmids containing immunogenic epitopes were selected. After identification of the putative open reading frames (ORFs) in these constructs, the *M. vaccae* fragments comprising only the ORF-portion were sub-cloned into pcDNA3-hGH' as described above. These plasmids were called DNA5, DNA9, DNA26, DNA27, DNA29, DNA37, DNA44 and DNA45. Three ORFs, referred to as A, B and C, were identified in DNA9. Open reading frames B and C were in the reverse orientation and were discarded. ORF A was cloned separately and the resulting plasmid was called DNA9A. The determined genomic DNA sequences of the inserts of DNA5, DNA9A, DNA26, DNA27, DNA29, DNA37, DNA42, DNA44 and DNA45 are given in SEQ ID NO: 13–21, respectively, with the predicted amino acid sequences of the corresponding ORFs being provided in SEQ ID NOS: 69–77, respectively. More than one epitope was identified in the inserts of the plasmids DNA5 and DNA27. These epitopes were not separated by cloning and were tested as multiple epitopes in all the assays. The determined genomic DNA sequences of epitope 1, epitope 2 and epitope 3 of DNA5, and of epitope 1 and epitope 2 of DNA27 are given in SEQ ID NOS: 8–12, respectively, with the corresponding predicted amino acid sequences being provided in SEQ ID NOS: 64–68, respectively. The determined epitope DNA sequences were compared to sequences in the EMBL DNA database using the FASTA computer algorithm. The corresponding predicted protein sequences (DNA translated to protein in each of 6 reading frames) were compared to sequences in the SwissProt database using the computer algorithm FASTX. Comparisons of DNA sequences provided in SEQ ID NO: 8–21 to sequences in the EMBL DNA database (using FASTA) and amino acid sequences provided in SEQ ID NOS: 64–77 to sequences in the SwissProt database (using FASTX) were made as of Mar. 21, 1999.

The predicted amino acid sequences of DNA5 epitope 2, DNA27 epitope 1, DNA9A, DNA29, DNA37, DNA44 and DNA45 (provided in SEQ ID NOS: 65, 67, 70, 73, 74, 76 and 77) were found to have less than 50% identity, determined as described above, to sequences in the SwissProt database using FASTX. The predicted amino acid sequences of DNA5 epitopes 1 and 3 (provided in SEQ ID NOS: 64 and 66) was found to have less than 75% identity, determined as described above, to sequences in the SwissProt database using FASTX. No matches were found to the predicted amino acid sequence of DNA27 epitope 2 and DNA26 (provided in SEQ ID NOS: 68 and 71). Table 1, below, shows the results of the comparison of the inventive amino acid sequences with those in the SwissProt database using FASTX as described above, wherein "No. of identical residues" represents the number of identical residues within the aligned portion.

TABLE 1

|  | SEQ ID NO: | Length (residues) | Length of alignment (residues) | No. of identical residues | % of identical residues |
|---|---|---|---|---|---|
| DNA5, epitope 1 | 64 | 13 | 11 | 8 | 61 |
| DNA5, epitope 2 | 65 | 32 | 31 | 10 | 32 |
| DNA5, epitope 3 | 66 | 26 | 25 | 14 | 53 |
| DNA9A | 70 | 75 | 68 | 24 | 32 |
| DNA26 | 71 | 97 | No Hits | | |
| DNA27, epitope 1 | 67 | 38 | 30 | 16 | 42 |
| DNA27, epitope 2 | 68 | 11 | No Hits | | |
| DNA29 | 73 | 46 | 40 | 17 | 37 |
| DNA37 | 74 | 87 | 80 | 26 | 32 |
| DNA44 | 76 | 44 | 35 | 17 | 38 |
| DNA45 | 77 | 59 | 52 | 21 | 35 |

EXAMPLE 2

EXPRESSION OF RECOMBINANT EPITOPES IN PROKARYOTIC AND EUKARYOTIC CELLS

Epitope DNA was subcloned into vectors for expression of polypeptides in bacterial and eukaryotic cells. The bacterial expression vector was a modified pET16 vector (Novagen, Madison, Wis.). Inserts from all the plasmids except for DNA9, were amplified with primers AD136 and AD133 (SEQ ID NO: 22 and 23, respectively) and cloned by blunt-end ligation into the pET16 vector that was EcoRI-digested and end-filled with DNA polymerase PfuI (Stratagene, La Jolla Calif.). The insert of DNA9A was amplified with AD250 and AD251 (SEQ ID NOS: 24 and 25, respectively) and cloned into the pET16 vector as described above.

To express the polypeptides in eukaryotic cells, the pcDNA3 vector (Invitrogen) was modified to include a histidine tag at the 3' end of the cloning site. This was done by cloning the double-stranded oligonucleotide AD180/AD181 into pcDNA3 digested with BamHI and EcoRI. The sequences of oligonucleotides AD180 and AD181 are given in SEQ ID NOS: 26 and 27, respectively. Plasmid inserts were amplified with the hGH-specific N-terminus 5' primer AD134 (SEQ ID NO: 28) and an epitope-specific 3' end primer, using the pcDNA3-hGH' constructs as DNA template. The sequences of the epitope-specific 3' primers AD151 (DNA5), AD153 (DNA26), AD154 (DNA27), AD155 (DNA29), AD158 (DNA42), AD159 (DNA44), AD160 (DNA45), AD167 (DNA37) and AD182 (DNA9) are listed in SEQ ID NO: 29–37, respectively.

This vector was again modified to remove excess sequence (42 nucleotides) between the hGH leader sequence and the expressed sequence, so that the hGH' sequence in this construct was reduced to the leader sequence and the first 5 N-terminal amino acids of the hGH sequence only. Using the pcDNA3-hGH3' construct as DNA template, the shortened fusion partner was amplified by PCR using primers AD105 (SEQ ID NO: 1) and AD222 (SEQ ID NO: 38). Cloning into pcDNA3-His was done at the HindIII and BamHI sites and the resulting construct was called pcDNA3-hGHls/His. The determined DNA sequence of the hGH-fusion partner cloned into pcDNA3-hGH-ls is given in SEQ ID NO: 39 and the corresponding amino acid sequence in SEQ ID NO: 78. The construct consisting of the insert from DNA9A was prepared by PCR amplification using primers AD223 and AD226 (SEQ ID NOS: 40 and 41, respectively).

EXAMPLE 3

IMMUNOGENICITY OF RECOMBINANT EPITOPE CONSTRUCTS

This example describes the results of immunogenicity studies performed with eight selected recombinant epitopes in either DNA or recombinant polypeptide form.

A. Stimulation of Human Peripheral Blood Mononuclear Cells (PBMC) to Proliferate and Secrete Interferon Gamma (IFN-γ) in vitro The recombinant epitopes (1 and 10 μg) expressed by the pET16 bacterial expression system were cultured with human PBMC at 37° C. After 48 hours, IFN-γ secretion was measured by enzyme-linked immunoassay (ELISA) following standard procedures. Parallel cultures were pulsed with tritiated thymidine and DNA synthesis was used to assess PBMC proliferation. For comparison, cells were also cultured with Purified Protein Derivative (PPD) from *M. tuberculosis* and with PBS as a negative control.

As shown in Table 2, all recombinant epitopes have the ability to stimulate IFN-γ production in at least some PBMC samples. Of the 12 PBMC samples tested, 10 were PPD positive, i.e., the PBMCs from these samples produced IFN-γ when cultured with PPD, and 2 were PPD-negative. PBMC responses were considered positive when the amount of IFN-γ produced was at least 3-fold higher than the IFN-γ produced by the PBS control samples. Recombinant epitopes 5 (corresponding to DNA5) and 44 (corresponding to DNA44) stimulated IFN-γ production in 100% of the PPD+ samples. Recombinant epitope 27 (corresponding to DNA27) stimulated IFN-γ production in 80% of the PPD+ samples. Recombinant epitopes 26 and 37 (corresponding to DNA26 and DNA37, respectively) stimulated IFN-γ production in 70% of the PPD+ samples, whereas epitope 45 (corresponding to DNA45) stimulated 20% PPD+ of the PBMC samples. PBMCs from PPD− samples did not respond significantly to any of the recombinant epitopes. This demonstrates that the epitopes are immunogenic in humans and trigger a recall response in samples from donors that were previously exposed to mycobacteria.

TABLE 2

Stimulation of IFN-γ production in human PBMC by recombinant epitopes

| Human PBMC | PBS control | PPD control | Recombinant Epitopes | | | | | |
|---|---|---|---|---|---|---|---|---|
| | | | 26 | 37 | 44 | 45 | 5 | 27 |
| G97022 | <0.1 | 0.16 | 0.3 | 0.3 | 0.4 | <0.1 | 0.5 | 0.1 |
| G97037 | <0.1 | 0.3 | 0.3 | 0.3 | 0.8 | 0.2 | 0.3 | 0.3 |
| G97001 | <0.1 | 4.5 | 0.6 | 1 | 3.5 | 0.2 | 1.8 | 1.7 |
| G97008 | <0.1 | 4.4 | 0.16 | 0.5 | 4 | <0.1 | 0.73 | 0.9 |
| G97011 | 0.25 | 4.9 | 0.9 | 0.5 | 1.2 | 0.25 | 2.8 | 1.2 |
| G97030 | <0.1 | 1.8 | 0.5 | 0.2 | 3.5 | 0.1 | 1.8 | 3 |
| G97033 | 0.12 | 4.5 | 0.5 | 0.25 | 3.4 | 0.2 | 1.7 | 1 |
| G97010 | <0.1 | >4 | >4 | >4 | >4 | 1 | >4 | >4 |
| G97028 | <0.1 | >4 | >4 | >4 | >4 | 1.2 | >4 | >4 |
| G97020 | <0.1 | 1 | 0.3 | 0.25 | >4 | <0.1 | 1.5 | 0.5 |
| G97032 | <0.1 | >4 | 0.5 | 1.2 | >4 | <0.1 | 1.4 | 0.5 |
| G97035 | <0.1 | 3.5 | 0.4 | 3.5 | >4 | <0.1 | 1 | 1 |

*Results are expressed as IFN-γ in ng/ml

Immunogenicity of the epitopes in humans was further demonstrated by the proliferative response of the human PBMC samples to both PPD and recombinant epitopes. The ability of the recombinant epitopes to stimulate PBMC proliferation was expressed as a stimulation index. A proliferation stimulus is considered positive when it is 5 times greater than the mean background proliferation produced by the medium-only control. As shown in Table 3, all recombinant epitopes were found to have the ability to stimulate PBMC proliferation in at least some of the human PBMC samples. Recombinant epitopes 26 and 27 stimulated PBMC proliferation in 92% of the samples, while recombinant epitopes 5, 37 and 44 stimulated proliferation in 83% of the samples. Epitope 45 stimulated PBMC proliferation in 17% of the samples. Stimulation of PBMC by PPD was 83%.

TABLE 3

Stimulation of PMBC proliferation

| Human PBMC | PPD | Recombinant epitopes | | | | |
|---|---|---|---|---|---|---|
| | | 5 | 26 | 27 | 37 | 44 | 45 |
| G97022 | 5* | 12 | 14 | 3 | 20 | 20 | 1 |
| G97037 | 35 | 12 | 25 | 20 | 15 | 30 | 1 |
| G97001 | 5 | 6 | 6 | 5 | 8 | 7 | 1 |
| G97008 | 60 | 20 | 30 | 15 | 40 | 60 | 2 |
| G97011 | 40 | 33 | 30 | 27 | 30 | 30 | 3 |
| G97030 | 100 | 140 | 120 | 140 | 120 | 140 | 30 |
| G97033 | 20 | 12 | 12 | 11 | 10 | 15 | 1 |
| G97010 | 2 | 4 | 2 | 6 | 2 | 4 | 2 |
| G97028 | 60 | 48 | 60 | 40 | 55 | 52 | 12 |
| G97020 | 10 | 10 | 10 | 8 | 10 | 10 | 1 |
| G97032 | 45 | 30 | 35 | 33 | 38 | 42 | 2 |
| G97035 | 3 | 4 | 5 | 6 | 3 | 4 | 2 |

*Results of human PBMC proliferation are expressed as Stimulation Index.

B. Immunization of Mice with DNA Epitopes

Protective immunity against subsequent infection with *M. tuberculosis* was induced in BALB/cByJ mice after injection of DNA encoding eight of the recombinant epitopes in pcDNA-hGH'/His or pcDNA3-hGHls/His constructs.

Induction of protective immunity was considered positive when a mean 0.5 log reduction in CFU in lung homogenates, compared to the mean CFUs from non-immunised control mice, was observed following subsequent infection with *M. tuberculosis*. A plasmid without an insert was used as control. The reduction in CFUs after epitope DNA immunisation was also compared with the known immunogenicity of *M. bovis* BCG. The results clearly show a reduction in CFUs in all the mice tested, suggesting the induction of protective immunity by the recombinant epitope DNA. In six of the groups, the reduction in CFUs was greater than 50% and in three of the groups the reduction was comparable to that induced by injection with *M. bovis* BCG.

TABLE 4

Protective immunity in mice induced by genetic immunisation with eight pcDNA-hGH'/His and pcDNA3-hGHls/His constructs

| Epitope construct | SEQ ID NO: | Number of Mice | Number of mice with reduced CFUs | % Mice with Reduced CFUs |
|---|---|---|---|---|
| Control plasmid | | 14 | 2 | 14 |
| DNA5 | 13 | 11 | 4 | 36 |
| DNA9 | 14 | 13 | 7 | 55 |
| DNA26 | 15 | 10 | 7 | 70 |
| DNA27 | 16 | 13 | 7 | 55 |
| DNA29 | 17 | 13 | 7 | 55 |
| DNA37 | 18 | 13 | 8 | 62 |
| DNA44 | 20 | 13 | 6 | 46 |
| DNA45 | 21 | 13 | 8 | 62 |
| *M. bovis* BCG | | 23 | 17 | 74 |

The induction of cytotoxic T lymphocytes (CTL), cytokines (IFN-γ, IL-4, IL-6 and IL-10), and proliferative and antibody responses upon genetic immunisation with eight pcDNA-hGH'/His or pcDNA3-hGHls/His constructs were assessed as follows.

CTL Assay

Cytolytic (CTL) activity in spleen cells of DNA-immunised BALB/cByJ mice was measured following a standard two-step procedure using the MHC haplotype matching target cells, BALB-3T3 (ATCC No. CRL-163, American Type Culture Collection, Manassas, Va.). Target cells were prepared by transfecting BALB/3T3 cells with eight pcDNA-hGH'/His or pcDNA3-hGHls/His epitope DNA constructs. Stably transfected cell lines were produced by geneticin selection (G418; Gibco BRL Life Technologies) and single cells were isolated by limiting dilution. Clones expressing epitopes were selected by RT-PCR using primers AD105 and AD181 (SEQ ID NOS: 1 and 27, respectively). Spleen cells of DNA-immunised mice were cultured in cDMEM enriched with 10% FCS in the presence of mytomycin-treated BALB-3T3 cells transfected with matching epitope DNA to re-stimulate cytotoxic T cells in vitro. Cultures were incubated at 37° C. under 10% $CO_2$ for 6 days. Cytolytic activities were monitored by incubating a fraction of each stimulated cell culture with DNA-matched target cells that were pulsed with $^{51}$Chromium, and measuring $^{51}$Chromium release in the supernatant of cell cultures. As shown in Table 5, specific CTL activity was detected in the spleens of mice immunised with four of the DNA constructs tested.

Cytokine and Proliferative Responses:

Cytokine production and proliferative responses of spleen cells from DNA-immunised BALB/cByJ mice were assessed following in vitro re-stimulation with recombinant epitopes. Cytokine and proliferative responses were measured by ELISA and 3H-thymidine pulse, respectively, as described above. As shown in Table 5, spleen cells from the six groups tested produced the Th1 cytokine IFN-γ. No Th2 cytokines (e.g. IL-4, IL-6 and IL-10) were detected in supernatants of stimulated cells. Proliferative responses were low and detected in spleen cells from two immunised groups only.

Antibody Responses

Blood samples from three DNA-immunised BALB/cByJ mice were collected two weeks after the last DNA injection and sera were prepared according to standard procedures. The presence of anti-epitope antibodies was determined by ELISA. The wells of a microtitre plate were coated with 500 ng of recombinant epitope. Antibody titres were measured by adding serial dilutions of serum into the wells. Bound antibodies were detected according to ELISA procedures as described above. As shown in Table 5, anti-epitope antibodies were detected in two blood samples tested. ELISA assays were also performed to determine whether the antibodies belonged to the IgG1 or IgG2a subclasses, using standard protocols. The results showed that the antibodies belonged to the IgG2a subclass, which is characteristic of a Th1 antibody response.

The data summarised in Table 5 indicate that immunisation with epitope DNA induced an immune response in mice. Furthermore, the cellular and humoral responses detected in the DNA-immunised mice demonstrated that a Th1 response was generated.

TABLE 5

Cytotoxic lymphocyte induction, cytokine responses, proliferation and antibody production induced in mice by genetic immunisation with eight PcDNA-hGH'/His or pcDNA3-hGHls/His constructs.

| Epitope constructs | SEQ ID NO: | CTL induction (% Specific lysis)* | Cytokine responses (IFN-γ in ng/ml)** | Proliferation (Stimulation Index) | Antibodies (titer) |
|---|---|---|---|---|---|
| DNA5 | 13 | 30 | 15 | not detected | not detected |
| DNA9A | 14 | 10 | NT*** | NT | NT |
| DNA26 | 15 | not detected | 30 | 7 | not detected |
| DNA27 | 16 | not detected | 33 | 3 | 1/100 |
| DNA29 | 17 | not detected | NT | NT | NT |
| DNA37 | 18 | not detected | 18 | not detected | not detected |
| DNA44 | 20 | 25 | 23 | not detected | 1/100 |
| DNA45 | 21 | 20 | 12 | not detected | not detected |

*Data shown is the mean % lysis from spleen cells of three mice. Non-specific lysis of control cells was deducted.
**Data shown is the mean IFN-γ in ng/ml obtained from triplicates of spleen cell cultures from three mice. Background IFN-γ produced by control cells was 5–7 ng/ml.
***NT = Not Tested

EXAMPLE 4

CLONING STRATEGY FOR *M. Vaccae* MULTI-EPITOPE CONSTRUCTS

The eight epitopes assayed in Example 4 were assembled to form multi-epitope constructs. Specifically, the DNA was amplified with primers containing a BglII 5'-extension and BamHI 3'-extension and was sequentially cloned into the BamHI site of pcDNA3/hGHls/His. The primers were AD223, AD226, AD229, AD230, AD231, AD232, AD233, AD234, AD235, AD236, AD256, AD258, AD259, AD260, AD261 and AD262 (SEQ ID NOS: 40–55, respectively).

The insert of plasmid DNA9A was cloned first into the BamHI site of pcDNA3-hGHls/His. The BamHI site of the vector was reconstituted at the 3' end of the cloning junction only and all other inserts except DNA5 were sequentially cloned into the same site. The insert of plasmid DNA5 was cloned last by blunt ligation into the end-filled BamHI site of pcDNA3-hGHls/His. Following this protocol, various combinations of epitopes were cloned into the pcDNA3-hGHls/His vector. The determined DNA sequences of three multi-epitope constructs consisting of 8-mer multi-epitopes (called ME/A, ME/B and ME/D) are shown in SEQ ID NOS: 56–58, respectively, and the predicted corresponding amino acid sequences in SEQ ID NOS: 79–81, respectively. Each one of these multi-epitope constructs includes each one of the 8 epitopes, but in a different order.

For expression of multi-epitope recombinant proteins in bacteria, the inserts of plasmids ME/A, ME/B and ME/D were subcloned into the modified expression vector pET16. All 8-mer epitope DNA combinations had DNA9A and DNA5 at the 5' and 3' end, respectively. The plasmid inserts were amplified using primers AD272 and AD273 (SEQ ID NOS: 59 and 60, respectively) and the purified amplified fragments cloned by blunt-end ligation into the pET16 vector that was EcoRI-digested and end-filled with DNA polymerase PfuI (Stratagene). Recombinant protein was expressed using *E. coli* host cells according to the manufacturer's protocol and purified using standard protocols.

Although the present invention has been described in some detail by way of illustration and example for purposes of clarity of understanding, changes and modifications can be carried out without departing from the scope of the invention which is intended to be limited only by the scope of the appended claims.

We claim:

1. A fusion protein comprising SEQ ID NO: 71.
2. The fusion protein of claim 1, wherein the fusion protein comprises SEQ ID NO: 79.
3. A composition comprising a fusion protein according to claim 2 and at least one component selected from the group consisting of physiologically acceptable carriers and non-specific immune response enhancers.
4. A method for enhancing an immune response in a patient, comprising administering to the patient a composition of claim 3.
5. A pharmaceutical composition comprising a fusion protein according to claim 1 and a physiologically acceptable carrier.
6. A method for the treatment of tuberculosis in a patient, comprising administering to the patient a pharmaceutical composition of claim 5.
7. A composition comprising a fusion protein according to claim 1 and a non-specific immune response enhancer.
8. A method of enhancing an immune response in a patient comprising administering to the patient a composition according to claim 7.
9. The method of claim 8, wherein the immune response is a Th1 response.
10. The method of claim 8, wherein the composition activates at least one cell selected from the group consisting of T cells and NK cells.
11. The method of claim 8, wherein the composition stimulates cytokine production.
12. The method of claim 8, wherein the composition induces long-term memory cells.
13. A method for the treatment of tuberculosis in a patient, comprising administering to the patient a composition of claim 7.
14. A method for the treatment of tuberculosis in a patient, comprising administering to the patient a composition of claim 3.
15. A method for enhancing an immune response in a patient, comprising administering to the patient a pharmaceutical composition according to claim 5.
16. The method of claim 15, wherein the immune response is a Th1 response.
17. The method of claim 15, wherein the pharmaceutical composition activates at least one cell selected from the group consisting of T cells and NK cells.
18. The method of claim 15, wherein the pharmaceutical composition stimulates cytokine production.
19. The method of claim 15, wherein the pharmaceutical composition induces long-term memory cells.
20. The fusion protein of claim 1, wherein the fusion protein comprises SEQ ID NO: 80.
21. A composition comprising a fusion protein according to claim 20 and at least one component selected from the group consisting of physiologically acceptable carriers and non-specific immune response enhancers.
22. A method for enhancing an immune response in a patient, comprising administering to the patient a composition of claim 21.
23. A method for the treatment of tuberculosis in a patient, comprising administering to the patient a composition of claim 21.
24. The fusion protein of claim 1, wherein the fusion protein comprises SEQ ID NO: 81.
25. A composition comprising a fusion protein according to claim 24 and at least one component selected from the group consisting of: physiologically acceptable carriers and non-specific immune response enhancers.
26. A method for enhancing an immune response in a patient, comprising administering to the patient a composition of claim 25.
27. A method for the treatment of tuberculosis in a patient, comprising administering to the patient a composition of claim 25.

* * * * *